US012637651B2

(12) United States Patent
Shum et al.

(10) Patent No.: US 12,637,651 B2
(45) Date of Patent: May 26, 2026

(54) MATERIAL METRIC MEASUREMENT

(71) Applicant: DEKA Products Limited Partnership, Manchester, NH (US)

(72) Inventors: Lauren N. Shum, Manchester, NH (US); David Blumberg, Jr., Deerfield, NH (US)

(73) Assignee: DEKA Products Limited Partneship, Manchester, NH (US)

( * ) Notice: Subject to any disclaimer, the term of this patent is extended or adjusted under 35 U.S.C. 154(b) by 1640 days.

(21) Appl. No.: 16/515,130

(22) Filed: Jul. 18, 2019

(65) Prior Publication Data
US 2020/0024566 A1      Jan. 23, 2020

Related U.S. Application Data

(60) Provisional application No. 62/847,281, filed on May 13, 2019, provisional application No. 62/700,313, filed on Jul. 18, 2018.

(51) Int. Cl.
| | |
|---|---|
| *A61B 5/053* | (2021.01) |
| *C12M 1/34* | (2006.01) |
| *C12M 1/36* | (2006.01) |
| *H01Q 7/04* | (2006.01) |
| *A61B 5/06* | (2006.01) |
| *A61N 1/36* | (2006.01) |

(52) U.S. Cl.
CPC ............ *C12M 41/32* (2013.01); *C12M 41/36* (2013.01); *C12M 41/48* (2013.01); *H01Q 7/04* (2013.01); *A61B 5/063* (2013.01); *A61N 1/3614* (2017.08)

(58) Field of Classification Search
CPC ....... C12M 41/36; C12M 41/32; G01R 27/06; G01R 29/0878; A61N 1/3614; A61B 5/063
See application file for complete search history.

(56) References Cited

U.S. PATENT DOCUMENTS

| | | | | |
|---|---|---|---|---|
| 5,583,432 A | * | 12/1996 | Barnes | ................... G01N 15/05 |
| | | | | 324/204 |
| 8,274,307 B1 | * | 9/2012 | Ben Artsi | .............. H01P 5/028 |
| | | | | 333/34 |
| 10,765,109 B1 | * | 9/2020 | Dev | ........................ A01G 7/06 |

(Continued)

OTHER PUBLICATIONS

Sabuncu et al., Microfluidic impedance spectroscopy as a tool for quantitative biology and biotechnology, Jul. 13, 2012, Biomicrofluidics, 034103, pp. 1-14. (Year: 2012).*

(Continued)

*Primary Examiner* — Alesa Allgood
(74) *Attorney, Agent, or Firm* — Mark E. Tetreault

(57) ABSTRACT

System and method for monitoring material change by measuring at least one metric. In a first configuration, an EM signal is transmitted across a calibrated transmission configuration to at least one load including the material, the reflection is measured, and the at least one metric is calculated based at least on the reflection. In a second configuration, an EM signal is transmitted in the vicinity of at least one resonator that is operably coupled with a load that can include the material. An EM signal is received that has been affected by the resonator, and a measurement of the at least one metric can be based at least on the received signal.

6 Claims, 27 Drawing Sheets

(56) References Cited

U.S. PATENT DOCUMENTS

| 2008/0231337 | A1* | 9/2008 | Krishnaswamy | ...... | H03K 3/537 |
| | | | | | 327/291 |
| 2015/0035546 | A1* | 2/2015 | Wang | ................ | G01N 15/1459 |
| | | | | | 324/638 |

OTHER PUBLICATIONS

"Appendix A: Brief introduction to bioimpedance" from "Electrical Impedance Tomography: Methods, History and Applications." Ed. Holder, David S., Institute of Physics, Series in medical Physics and Biomedical Engineering, IOP Publishing Ltd, ISBN: 0 7503 0952, 2005.

"Determination of Cell Confluence using Automated Cell Imaging for Verification of Cell Retention during Rigorous Cell Washing" in BioTek Tech Note from BioTek Instruments, Inc., www.biotek.com, Rev. Dec. 18, 2017.

"Combining optical and electrical impedance techniques for quantitative measurement of confluence in MDCK-I cell cultures" by Birgitte Freiesleben De Blasio, Morten Laane, Thomas Walmann, and Ivar Giaever. in: BioTechniques 36:650-662 (Apr. 2004).

"Cell Line Classification Using Electric Cell-substrate Impedance Sensing (ECIS)" by Megan L. Gelsinger, Laura L. Tupper, and David S. Matteson, Oct. 27, 2017.

"Organs-on-chips with integrated electrodes for trans-epithelial measurements of human epithelial barrier function" by Oliver Y.F. Henry, Remi Villenave, Michael J. Cronce, William D. Leineweber, Maximilian A. Benz and Donald E. Ingber, from Lab Chip May 26, 2017, ©Royal Society of Chemistry.

"A Biosensor that Monitors Cell Morphology with Electrical Fields" by Charles R. Keese and Ivar Giaever, from IEEE Enigneering in Medicine and Biology, Jun./Jul. 1994.

"Organs-on-Chips with combined multi-electrode array and transepithelial electrical resistance measurement capabilities" by Ben M. Maoz, Anna Herland, Oliver Y. F. Henry, William D. Leineweber, Moran Yadid, John Doyle, Robert Mannix, Ville J. Kujala, Edward A. FitzGerald, Kevin Kit Parker, and Donald E. Ingber, from Lab Chip, 2017.17.2294-2302, ©Royal Society of Chemistry 2017.

"Electric Field Imaging" by Joshua Reynolds Smith, submitted in partial fulfillment of the requirements for the degree of Doctor of Philosophy at MIT, Nov. 24, 1998, ©MIT 1999.

"TEER measurement techniques for in vitro barrier model systems" by Balaji Srinivasan, Aditya Reddy Kolli, Mandy Brigitte Esch, Hasan Erbil Abaci, Michael L. Shuler, and James J. Hickman, Author Manuscript *J Lab Autom.* Apr. 2015.

"Microwave Resonator for Eye Tracking" by Chieh-Sen Lee, Bin Bai, Qin-Rui Song and Guo-fen Li, IEEE MIT-S International Microwave Symposium (IMS 2019, Boston, MA Jun. 2-7, 2019.

"Electrick: Low-Cost Touch Sensing Using Electric Field Tomography" by Yang Zhang, Gierad Laput, Chris Harrison, Human-Computer Interaction Institute, Carnegie Mellon University, CHI 2017, May 6-11, 2017.

* cited by examiner

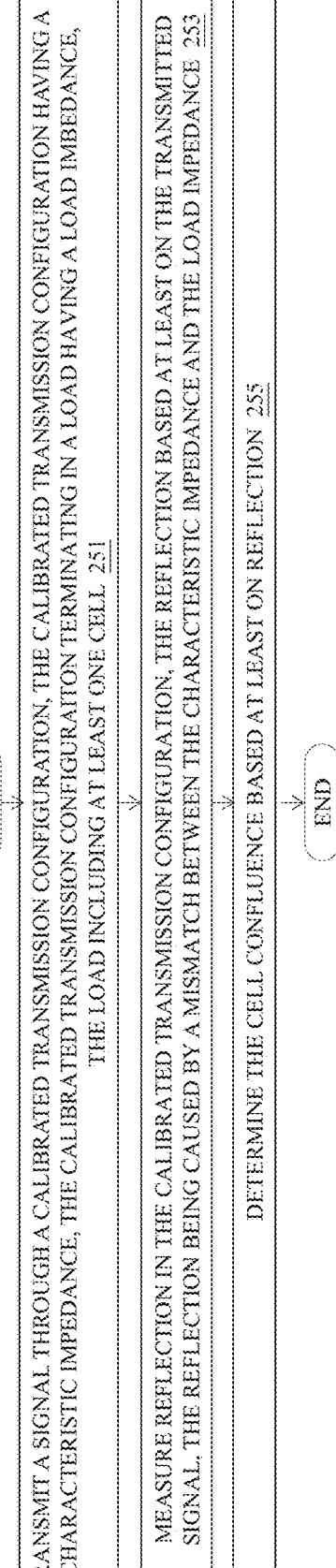

250

START

TRANSMIT A SIGNAL THROUGH A CALIBRATED TRANSMISSION CONFIGURATION, THE CALIBRATED TRANSMISSION CONFIGURATION HAVING A CHARACTERISTIC IMPEDANCE, THE CALIBRATED TRANSMISSION CONFIGURAITON TERMINATING IN A LOAD HAVING A LOAD IMBEDANCE, THE LOAD INCLUDING AT LEAST ONE CELL 251

MEASURE REFLECTION IN THE CALIBRATED TRANSMISSION CONFIGURATION, THE REFLECTION BASED AT LEAST ON THE TRANSMITTED SIGNAL, THE REFLECTION BEING CAUSED BY A MISMATCH BETWEEN THE CHARACTERISTIC IMPEDANCE AND THE LOAD IMPEDANCE 253

DETERMINE THE CELL CONFLUENCE BASED AT LEAST ON REFLECTION 255

END

FIG. 4

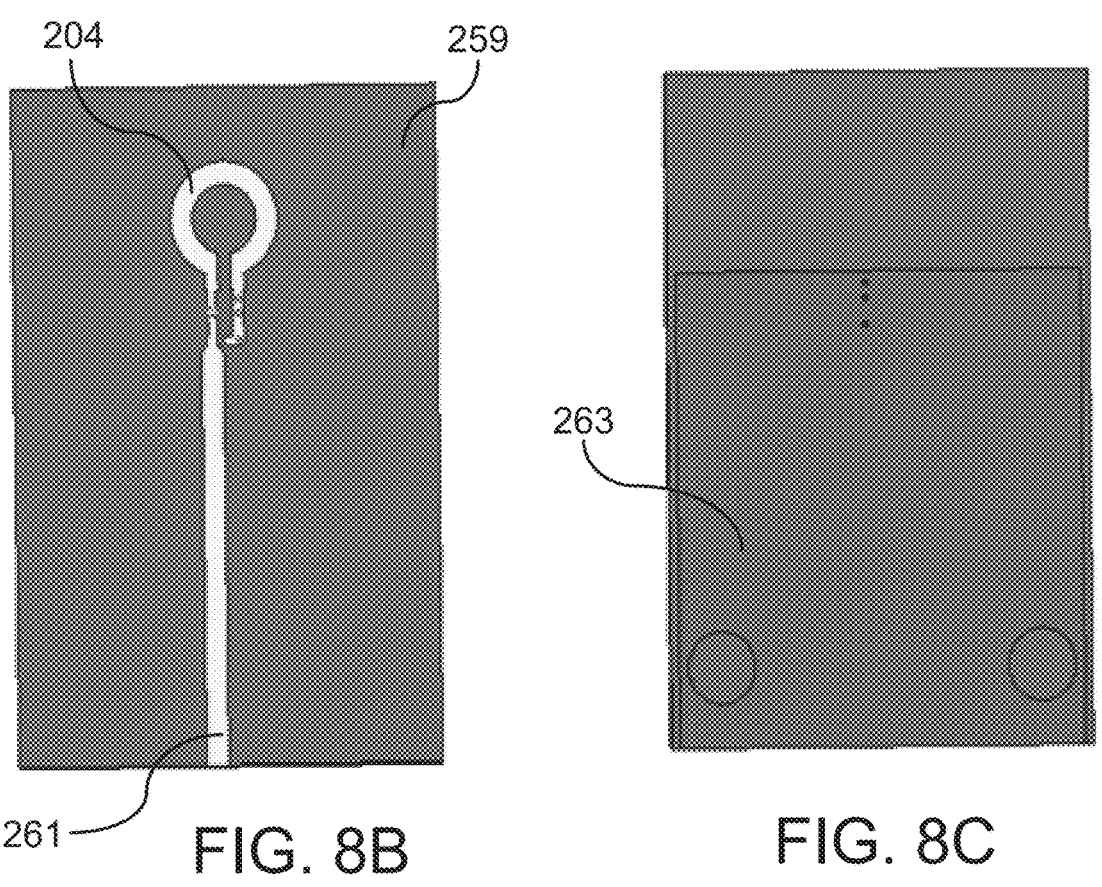
FIG. 8B
FIG. 8C
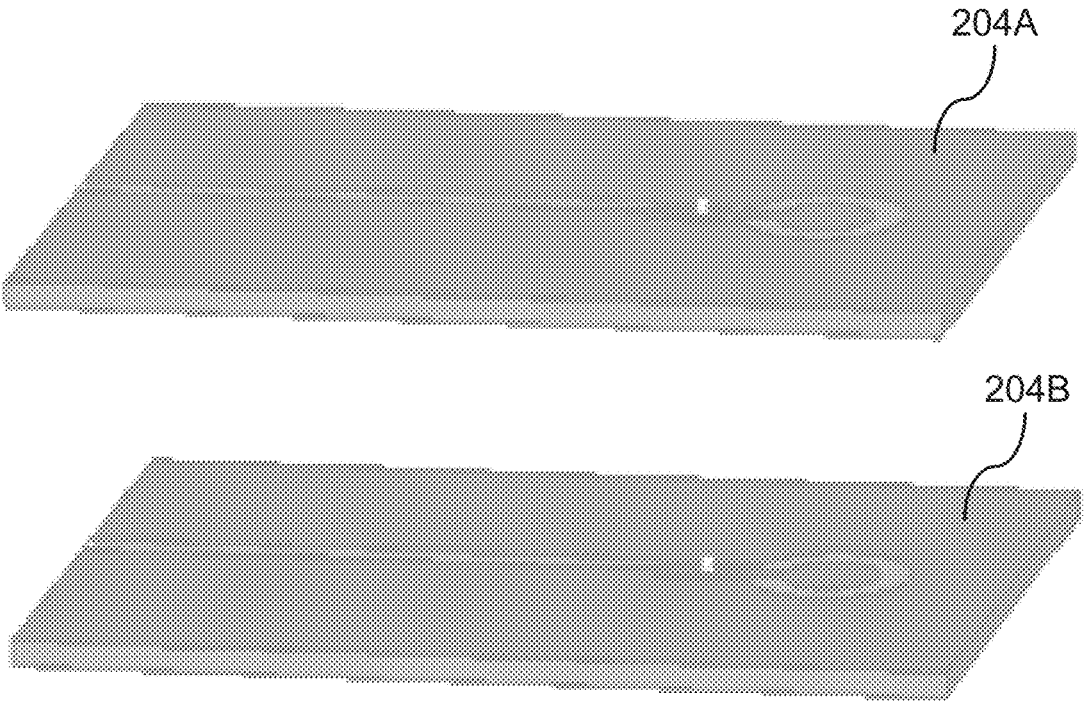
FIG. 8D

201A

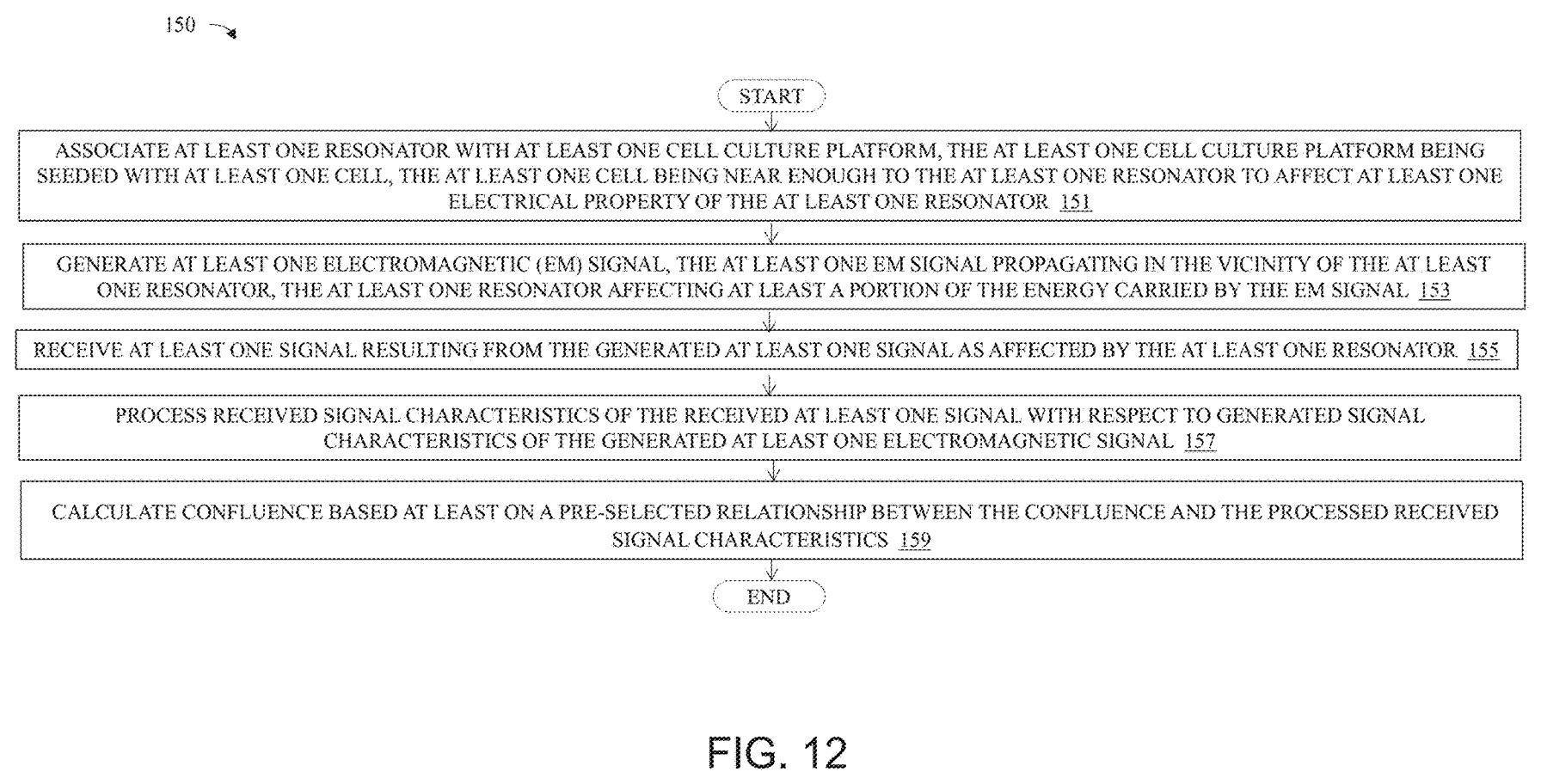

150

START

ASSOCIATE AT LEAST ONE RESONATOR WITH AT LEAST ONE CELL CULTURE PLATFORM, THE AT LEAST ONE CELL CULTURE PLATFORM BEING SEEDED WITH AT LEAST ONE CELL, THE AT LEAST ONE CELL BEING NEAR ENOUGH TO THE AT LEAST ONE RESONATOR TO AFFECT AT LEAST ONE ELECTRICAL PROPERTY OF THE AT LEAST ONE RESONATOR 151

GENERATE AT LEAST ONE ELECTROMAGNETIC (EM) SIGNAL, THE AT LEAST ONE EM SIGNAL PROPAGATING IN THE VICINITY OF THE AT LEAST ONE RESONATOR, THE AT LEAST ONE RESONATOR AFFECTING AT LEAST A PORTION OF THE ENERGY CARRIED BY THE EM SIGNAL 153

RECEIVE AT LEAST ONE SIGNAL RESULTING FROM THE GENERATED AT LEAST ONE SIGNAL AS AFFECTED BY THE AT LEAST ONE RESONATOR 155

PROCESS RECEIVED SIGNAL CHARACTERISTICS OF THE RECEIVED AT LEAST ONE SIGNAL WITH RESPECT TO GENERATED SIGNAL CHARACTERISTICS OF THE GENERATED AT LEAST ONE ELECTROMAGNETIC SIGNAL 157

CALCULATE CONFLUENCE BASED AT LEAST ON A PRE-SELECTED RELATIONSHIP BETWEEN THE CONFLUENCE AND THE PROCESSED RECEIVED SIGNAL CHARACTERISTICS 159

END

FIG. 12

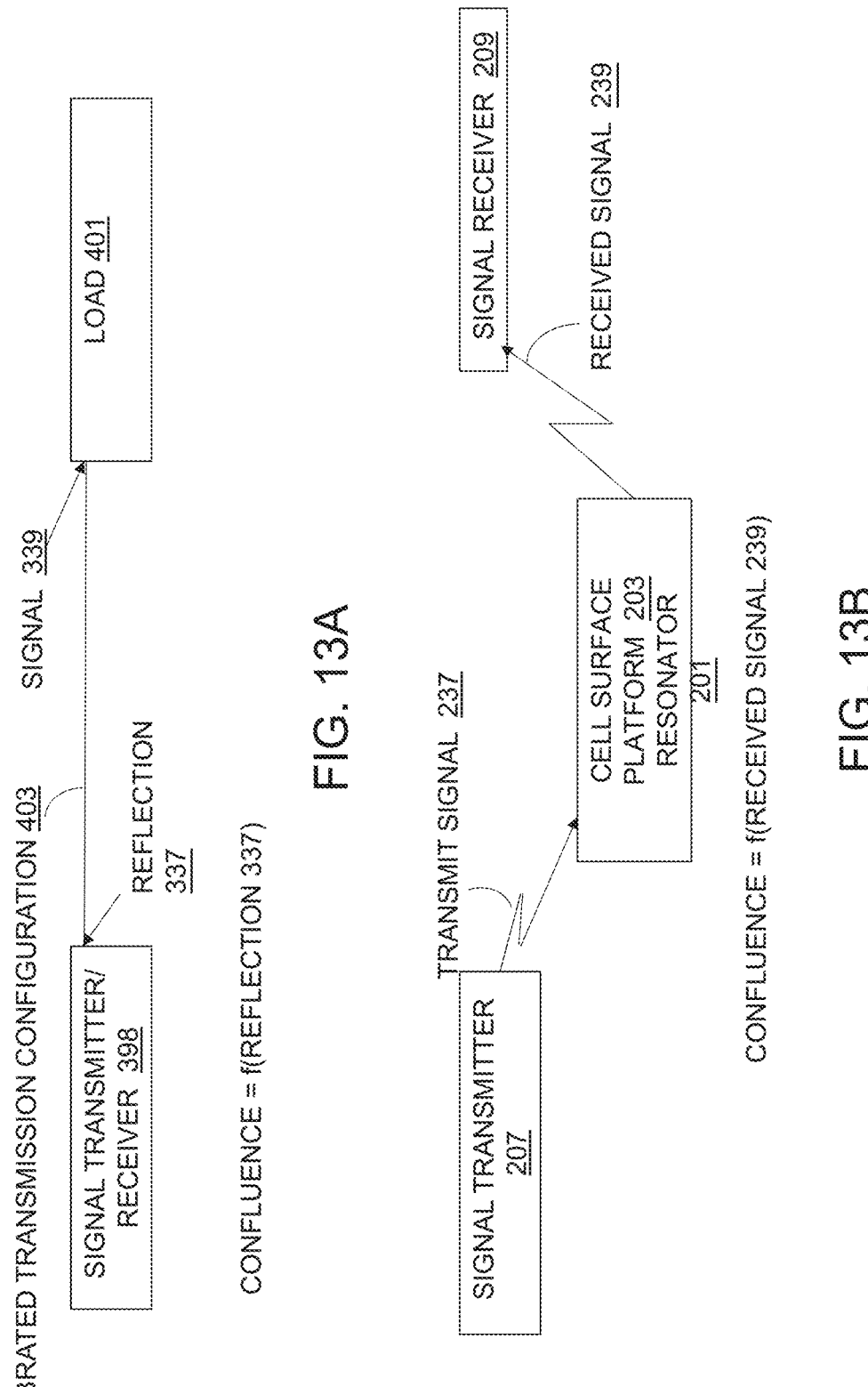

MATERIAL METRIC MEASUREMENT

CROSS REFERENCE TO RELATED APPLICATIONS

This utility patent application claims the benefit of U.S. Provisional Patent Application Ser. No. 62/700,313 filed Jul. 18, 2018, entitled Cell Confluence Measurement, and U.S. Provisional Patent Application Ser. No. 62/847,281 filed May 13, 2019, entitled Material Metric Measurement, which are incorporated herein by reference in their entirety.

GOVERNMENT LICENSE RIGHTS

This invention was made with government support under W911NF-17-3-003, subaward T0154, awarded by Advanced Regenerative Manufacturing Institute. The government has certain rights in the invention.

BACKGROUND

The present teachings relate generally to automated measurement, and more specifically to systems and methods for monitoring and measuring at least one metric of a material. In some configurations, the material can include cells and the at least one metric can include confluence.

One of the key technological gaps hindering the scale-up of adherent cell culture is the lack of automated, non-optical cell confluence measurement systems. While 3D culture vessels are being used to scale up cell expansion production quantities, there is no consistent, quantitative method for measuring confluence, a critical monitoring parameter, within these vessels. A wireless, impedance-based sensor for non-invasively tracking cell growth and confluence, which could be integrated into existing, state-of-the-art culture vessels can address this gap.

Controlling cell expansion is necessary for all tissue engineering processes to provide the desired quantities and phenotypes of cells for building tissues. Confluence (the percent of available growth area covered by cells) is a metric used to estimate when cells should be harvested in an expansion process. Over-confluent cells (i.e., cells that are too densely cultured) may change phenotype or even die off. However, to maximize expansion efficiency, cells should be grown until they occupy as much available space as possible without becoming over-confluent. The optimal confluence for harvesting most cell types during expansion is about 80%.

The current state of the art for measuring confluence is via optical image processing, but typically, it is qualitatively determined by laboratory researchers and technicians who estimate coverage as viewed in a microscope. Both optical and manual techniques are inherently low throughput and limited to 2D cell culture. State-of-the-art culture vessels, like multi-layer flasks and other 3D culture systems, increase expansion throughput and efficiency by increasing the available surface area for cells to grow on. However, the increased surface area obtained in these vessels is typically at the expense of optical access, making it impossible to measure cell growth throughout an entire 3D system. In a multi-layer flask, for example, only the bottom layer is observable with a typical inverted microscope, and the status of successive layers must be inferred. Though flask confluence is a critical variable in adherent cell culture, techniques for measuring it remain largely manual, qualitative, and imprecise. Developing quantitative measurement methods for cell confluence within 3D culture vessels is a key to scaling and automating the cell culture process for manufacturability.

SUMMARY

Electrical material measurement technology presents a manufacturing innovation because its compatibility with 3D culture geometries can eliminate a critical roadblock to using modern culture vessels for mass-producing materials, including cells, a necessary step on the road to scaling tissue engineering products. It can enable researchers, for the first time, to overcome the guesswork previously inherent to cell expansion. Electrical metric measurement technology can replace manual metric measurement, including, but not limited to, cell growth monitoring, with an automated process, removing another scaling obstacle and laying the foundation for additional automation. Wireless transmission can dramatically expand the bounds of scalability, because it can result in a non-invasive measurement that is not limited by the number of wires that must be connected to a cell culture vessel. The logistical simplicity of a wireless approach can ease its integration into existing 3D culture vessels, speeding up adoption.

The impedance of a medium describes the degree to which electromagnetic energy is obstructed as it passes through the medium. The impedance of most materials, including cells, varies with frequency. Furthermore, when electromagnetic (EM) energy crosses a boundary with an impedance mismatch, reflections occur. The systems and methods of the present teachings make use of these principles to measure at least one metric, including, but not limited to, cell confluence, automatically.

The method and system of the present teachings for measuring at least one metric of at least one load that is accumulating or shedding material can include, but are not limited to including, transmitting a signal through a calibrated transmission configuration. The calibrated transmission configuration can include a characteristic impedance, and the calibrated transmission configuration can terminate in at least one load having a load impedance. The at least one load can include the material. The method can include measuring reflection in the calibrated transmission configuration. The reflection can be based at least on the transmitted signal, and the reflection can be caused by an impedance mismatch between the characteristic impedance and the load impedance. The method can include determining the at least one metric based at least on the reflection associated with the at least one load.

The system and method of the present teachings can sense liquid levels and can sense object position change, discriminating displacements smaller than a thousandth of an inch. The system and method of the present teachings for determining a height of a fluid, where the fluid rests on a surface of a vessel, can include, but are not limited to including, generating at least one first EM signal, and transmitting the at least one first EM signal into a resonator. The resonator can be fixed into the vessel, the EM signal can create an EM field, and at least some portion of the EM field can propagate into the fluid. The method can include receiving at least one second signal resulting from the generated at least one first EM signal as affected by the at least one resonator and the height of the fluid. The method can include processing received signal characteristics of the received at least one second signal with respect to generated signal characteristics of the generated at least one first EM signal, and calculating the height based at least on the processed received signal characteristics. The height can optionally include a range of about 0.01 to 2 cm.

The system and method of the present teachings for sensing position and displacement of an object residing in a first position can include, but are not limited to including, (a) embedding at least one resonator in the object, and (b) positioning an antenna in proximity to the at least one resonator. The antenna position can be selected based at least on the position of the resonator. The method can include (c) transmitting at least one first EM signal through the antenna. The at least one resonator can interact with at least a portion of the EM signal, and the interaction between the at least one resonator and at least a portion of the EM signal can be affected by the antenna position. The method can include (d) receiving at least one second signal resulting from the generated at least one first EM signal as affected by the at least one resonator and the antenna position, (e) processing second signal characteristics associated with the at least one second signal with respect to first signal characteristics associated with the at least one first EM signal, and (f) moving the object to a second position. The method can include (g) repeating steps (a)-(e), and (f) calculating the displacement based at least on the processed second signal characteristics of the object in the first position and the processed second signal characteristics of the object in the second position.

BRIEF DESCRIPTION OF THE DRAWINGS

The present teachings will be more readily understood by reference to the following description, taken with the accompanying drawings, in which:

FIG. 4 is a flowchart of the first configuration method of the present teachings;

FIGS. 8A-8D-5 are pictorial and photographic diagrams of configurations of the antenna of the present teachings;

FIG. 12 is a flowchart of the second configuration method of the present teachings; and FIGS. 13A and 13B are schematic block diagrams that compare the first configuration confluence measurement system to the second configuration confluence measurement system.

DETAILED DESCRIPTION

Figure 1:
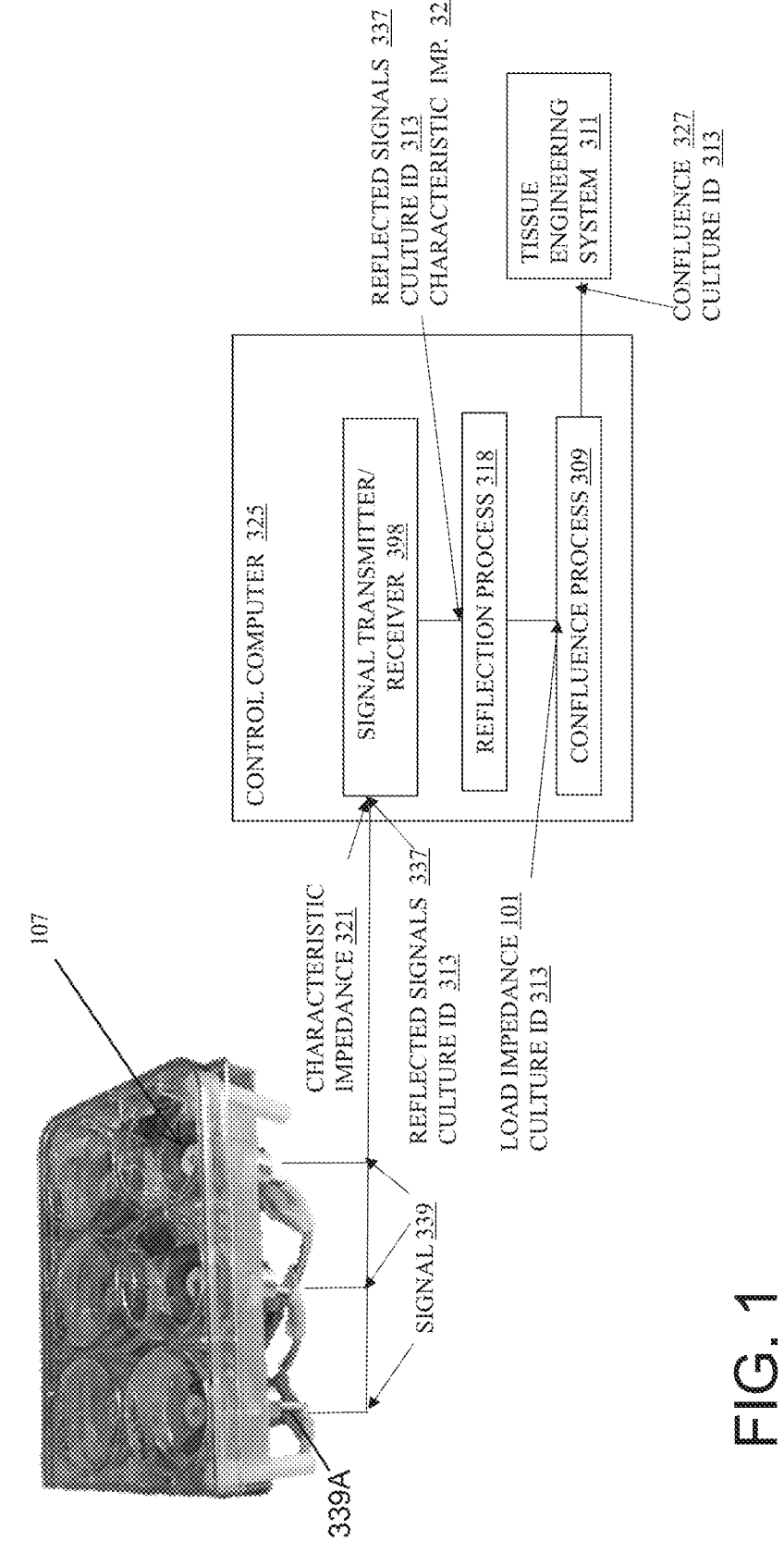
FIG. 1 is a schematic block diagram of the first configuration system of the present teachings.

Referring now primarily to FIG. 1, first configuration confluence system 125 can determine confluence 327 of the cells in load 401 (FIG. 13A), where load 401 (FIG. 13A) can include cells 119 (FIG. 2) and media, for example, but not limited to, cell growth media. Probe signals 339 can be transmitted through calibrated transmission configuration 403 (FIG. 13A) that can have characteristic impedance 321. When probe signals 339 encounter load 401 (FIG. 13A), which can present an impedance mismatch between characteristic impedance 321 of calibrated transmission configuration 403 (FIG. 13A) and load 401 (FIG. 13A), reflection signals 337, traveling in the opposite direction of probe signals 339, can result. First configuration confluence system 125 can include at least one confluence probe 107 and control computer 325, which can be operably coupled with each other by calibrated transmission configuration 403 (FIG. 13A). In some configurations, calibrated transmission configuration 403 (FIG. 13A) can include, but is not limited to including, a transmission line having two ends. A first end can be operably coupled with at least one confluence probe 107 through a first connector 339A. The transmission line and the at least one confluence probe can be configured to maintain a desired impedance. A second end can be operably coupled with the control computer 325 through a second connector (not shown). At least one confluence probe 107 can include, but is not limited to including, load 401 (FIG. 13A) which can include, but is not limited to including, cells 119 (FIG. 2) and media. At least one confluence probe 107 can be associated with culture identification (ID) 313. The use of culture ID 313 can enable load-dependent processing of various types of loads 401 (FIG. 13A), including various types of cells 119 (FIG. 2) and various timings of seeding the cells 119 (FIG. 2).

Continuing to refer to FIG. 1, control computer 325 can include, but is not limited to including, signal transmitter/receiver process 398, reflection process 318, and confluence process 309. Signal transmitter/receiver process 398 can initiate sending probe signals 339 across calibrated transmission configuration 403 (FIG. 13A). As probe signals 339 encounter cells 119 (FIG. 2) and media, and as reflected signals 337 travel across calibrated transmission configuration 403 (FIG. 13A), signal transmitter/receiver process 398 can receive reflected signals 337. Reflected signals 337 can, at least in part, be responsive to load 401 (FIG. 13A), and can represent a discontinuity (mismatch) in characteristic impedance 321 of calibrated transmission configuration 403 (FIG. 13A). Signal transmitter/receiver process 398 can provide reflected signals 337, culture ID 313, and characteristic impedance 321 to reflection process 318. Reflection process 318 can associate culture identification 313 with reflected signals 337, can determine load impedance 101, for example, and can provide those data to confluence process 309. Confluence process 309 can determine confluence 327 for the culture identified by culture ID 313 based at least on a pre-selected relationship between reflected signals 337 and confluence 327. Confluence process 309 can optionally provide confluence 327 and culture ID 313 to tissue engineering system 311. Tissue engineering system 311 can have an interest in the status of growing cells for reasons including, but not limited to, preventing cells from becoming overconfluent and monitoring cell growth with respect to environmental drivers such as, for example, temperature and nutrition. Other types of processes can be executed in control computer 325, and steps can be accomplished in an order different from the order set out herein.

Figure 2:
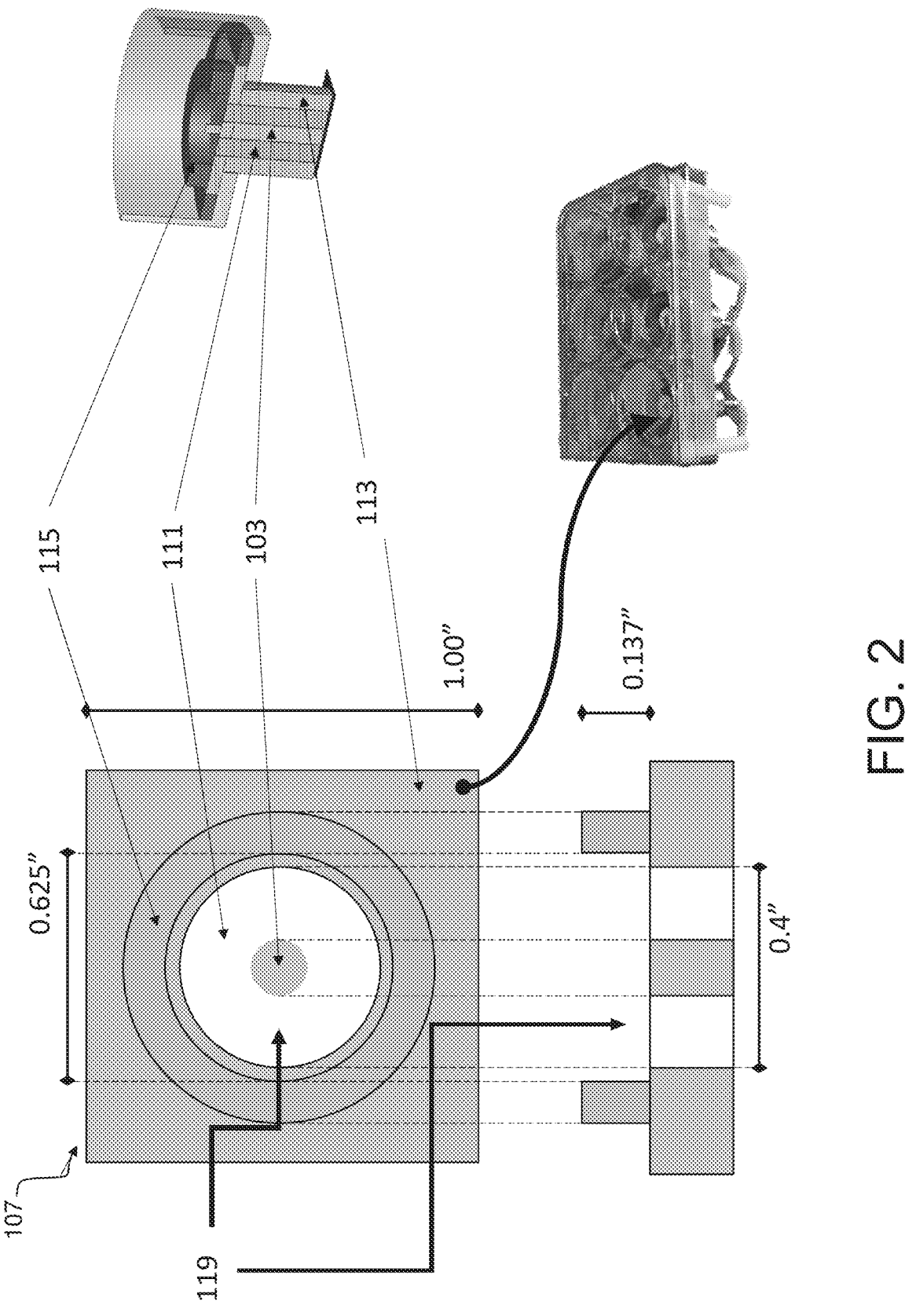
FIG. 2 is a pictorial depiction of a first configuration system of the present teachings for measuring the confluence of cells.

Referring now to FIG. 2, confluence probe 107 can provide an environment for cells to be seeded, to be nourished, and to reproduce, and for cell reproduction to be monitored. When probe signal 339 (FIG. 1) crosses a boundary in which there is an impedance mismatch, reflections 337 (FIG. 1) of probe signal 339 (FIG. 1) can occur. The impedance mismatch can occur between calibrated transmission configuration 403 (FIG. 13A) and load impedance 101 (FIG. 1), which can include, for example, but not limited to, cells 119 and media. Calibrated transmission configuration 403 (FIG. 13A) can include inner electrode 103 and outer electrode 113, and can be calibrated to maintain characteristic impedance 321 (FIG. 1) across a spectrum of frequencies. In some configurations, characteristic impedance 321 (FIG. 1) can be, for example, but not limited to, 50Ω, and in some configurations, characteristic impedance 321 (FIG. 1) can be, for example, but not limited to, 75Ω. Reflected signals 337 (FIG. 1), that can be based at least on transmitted probe signal 339 (FIG. 1), can be measured to determine confluence 327 (FIG. 1). When probe signal 339 (FIG. 1) is swept across a spectrum of frequencies, a frequency-varying characteristic curve, for example, impedance graph 105 (FIG. 3) of impedance as it varies with frequency, can be generated. Performing this sweep at different points during the cell growth process can identify impedance changes that can be used to determine cell confluence.

Continuing to refer primarily to FIG. 2, confluence probe 107 can include inner electrode 103, insulating material core 111, well edge 115, and outer electrode 113. Inner electrode 103, insulating material core 111, and outer electrode 113 can be provided by, but are not limited to being provided by, a conventional device such as, for example, but not limited to, an N-type straight jack flat tab 50Ω RF connector such as, for example, but not limited to AMPHENOL® flange #172195 (https://www.amphenolrf.com/172195.html). Inner electrode 103 can include, but is not limited to including, a material that can provide for corrosion resistance, strength, wear resistance, and stiffness of inner electrode 103. The material can include, but is not limited to including, phosphor bronze. Insulating material core 111 can include, for example, but is not limited to including, an abundant material that has a low dielectric constant such as, for example, but not limited to, TEFLON®. Well edge 115 can confine cells 119 and media, and can be constructed of a non-reactive material such as, for example, but not limited to, silicone. Insulating material core 111 can provide a surface upon which cells 119 can grow. Cells 119 and media can be placed in confluence probe 107, atop inner electrode 103 and insulating material core 111. Impedance changes over time, at the boundary between inner electrode 103 and cells 119 and media as cells grow, can be detected and can be used to compute cell confluence 327 (FIG. 1).

Figure 3:
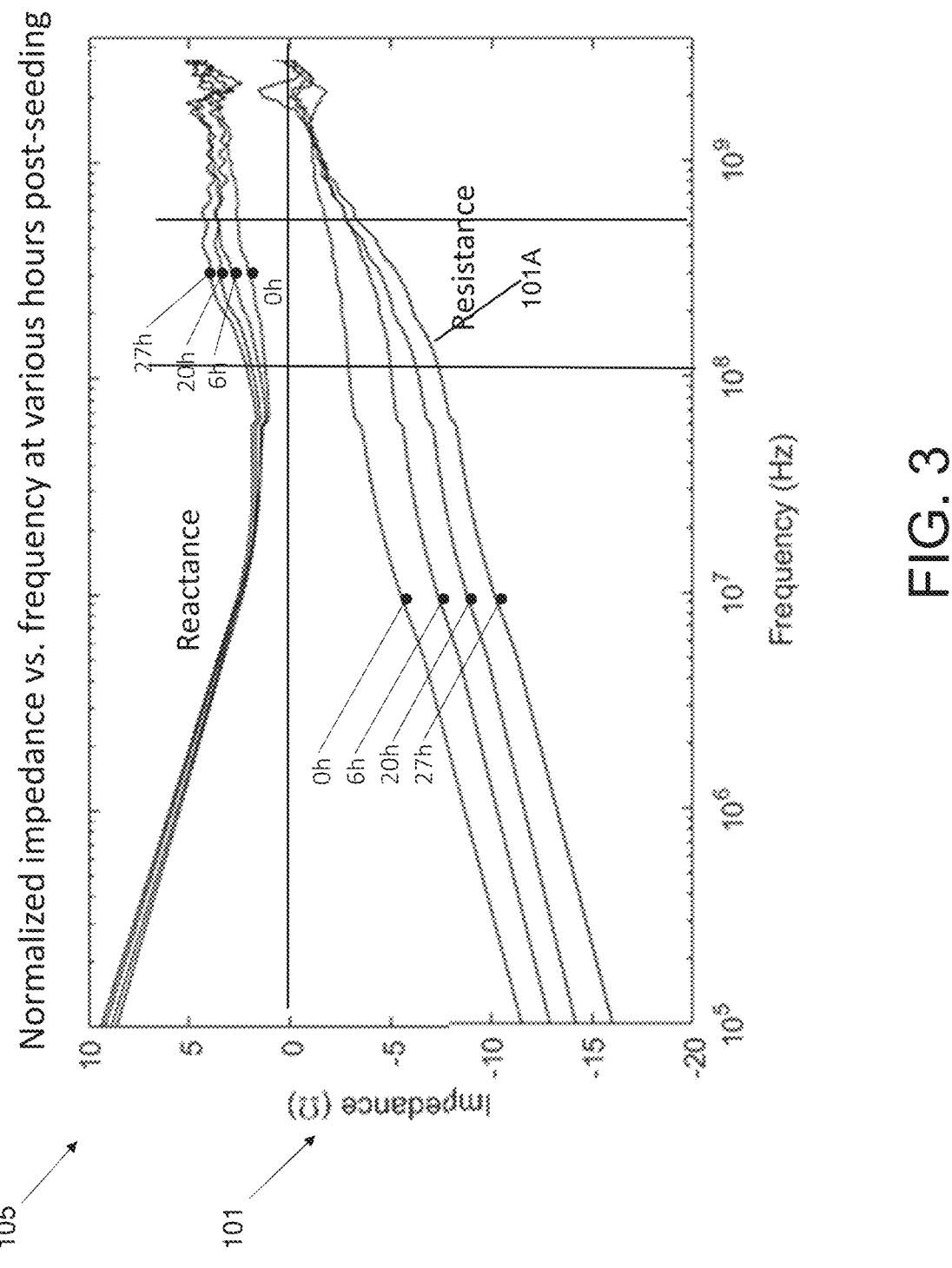
FIG. 3 is graphical depiction of the impedance results of the first configuration system of the present teachings.

Referring now to FIG. 3, as time progresses and cells 119 (FIG. 2) proliferate, trends can be identified such as, for example, but not limited to, an increase in the magnitude of load impedance 101. In some configurations, cells 119 can grow in a mixture with media, for example, for nourishment. Both cells 119 (FIG. 2) and media can contribute to load impedance 101. To isolate the impedance due to the presence and growth of cells 119 (FIG. 2), load impedance 101 can be normalized by subtracting the impedance measurement resulting from media alone from that obtained for cells 119 (FIG. 2) and media together. In some configurations, a confluence-based trend, herein related to elapsed time, since the cells multiply and become more numerous with increasing elapsed time, can emerge. For example, a time-based trend 101A in resistance has been identified empirically at frequencies under 100 MHz, and in reactance at frequencies between about 100 and 400 MHz.

Figure 8A:
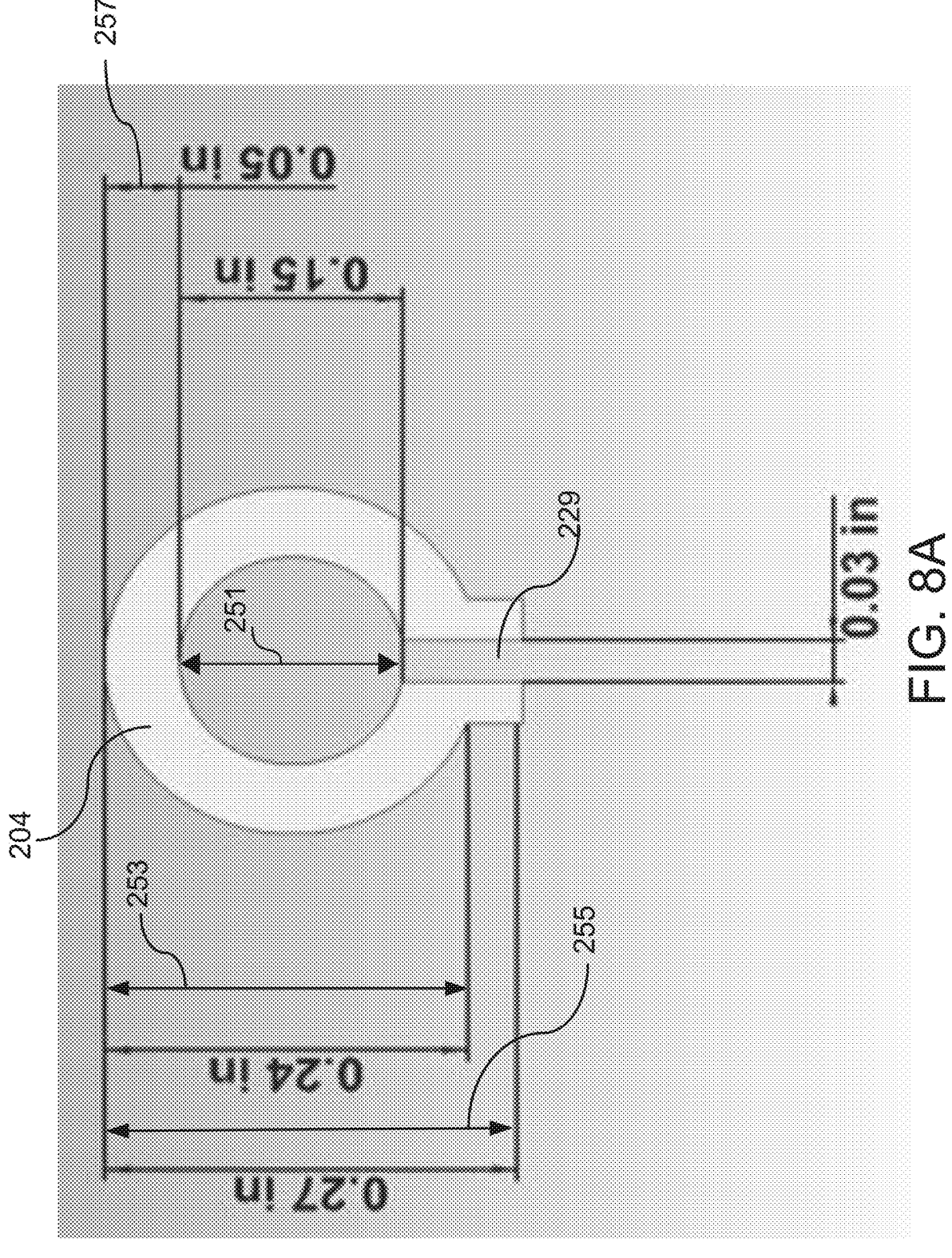
Figures 1, 8A:
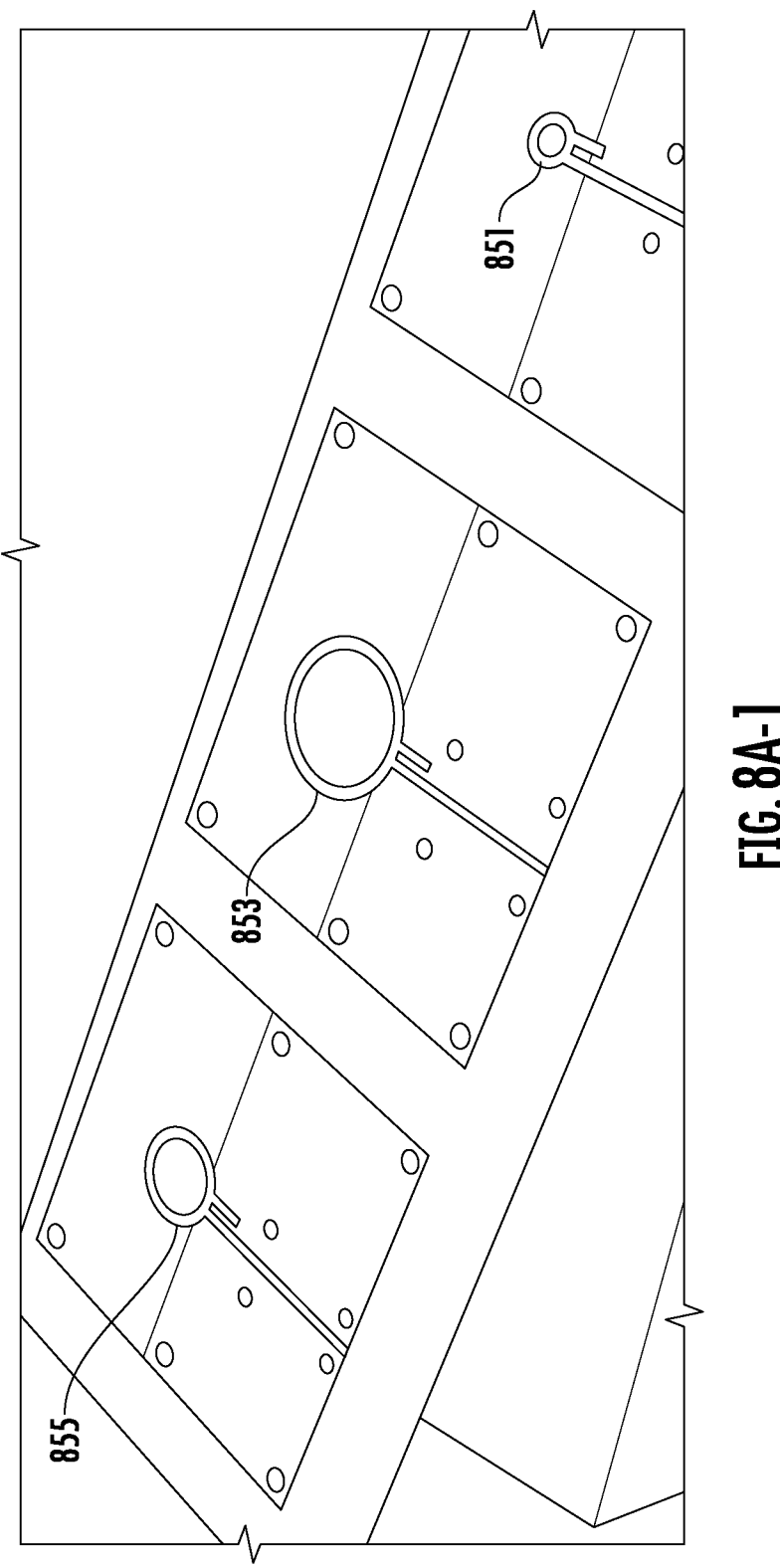
Figures 2, 8A:
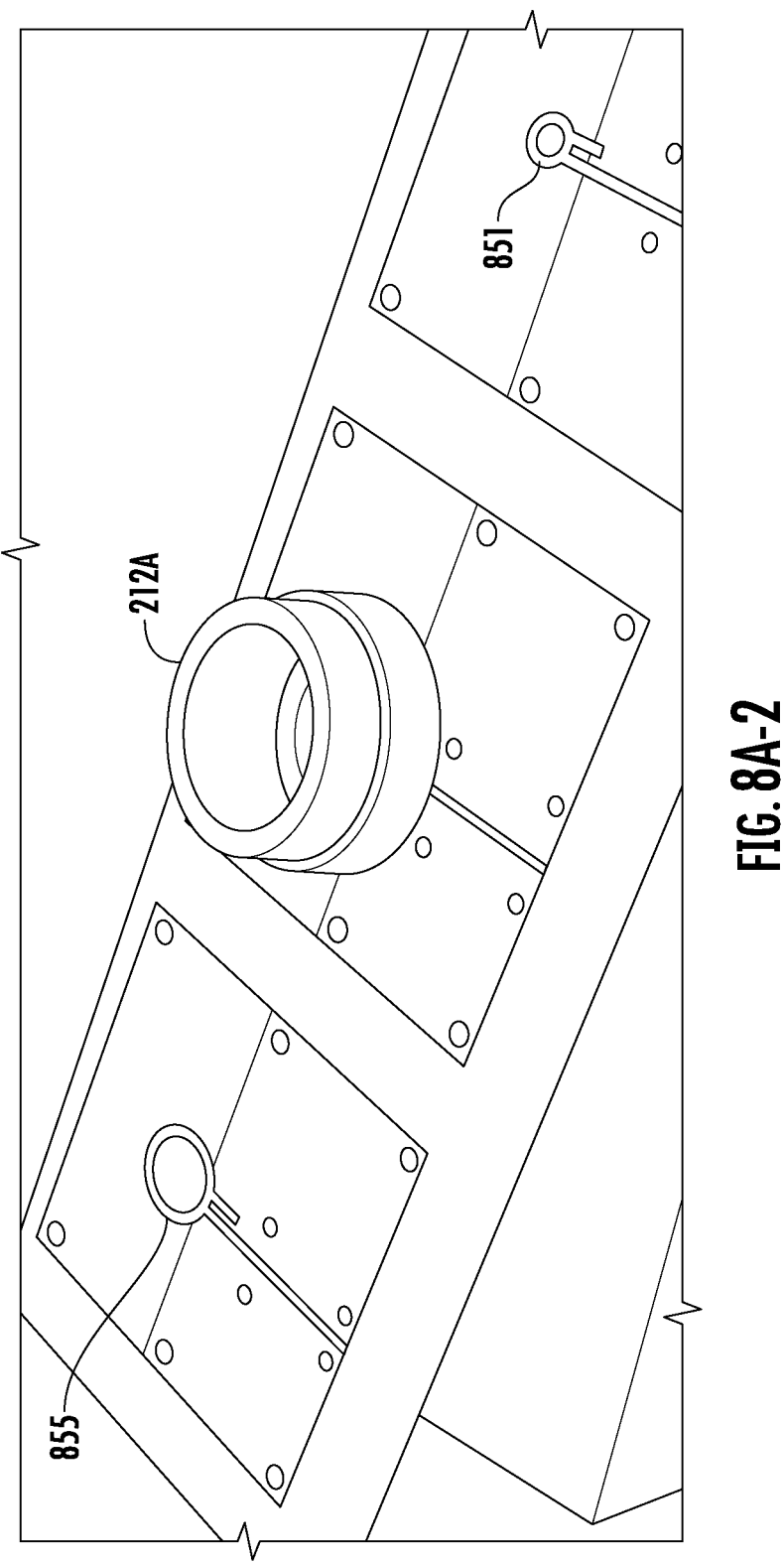
Figures 1, 8D:
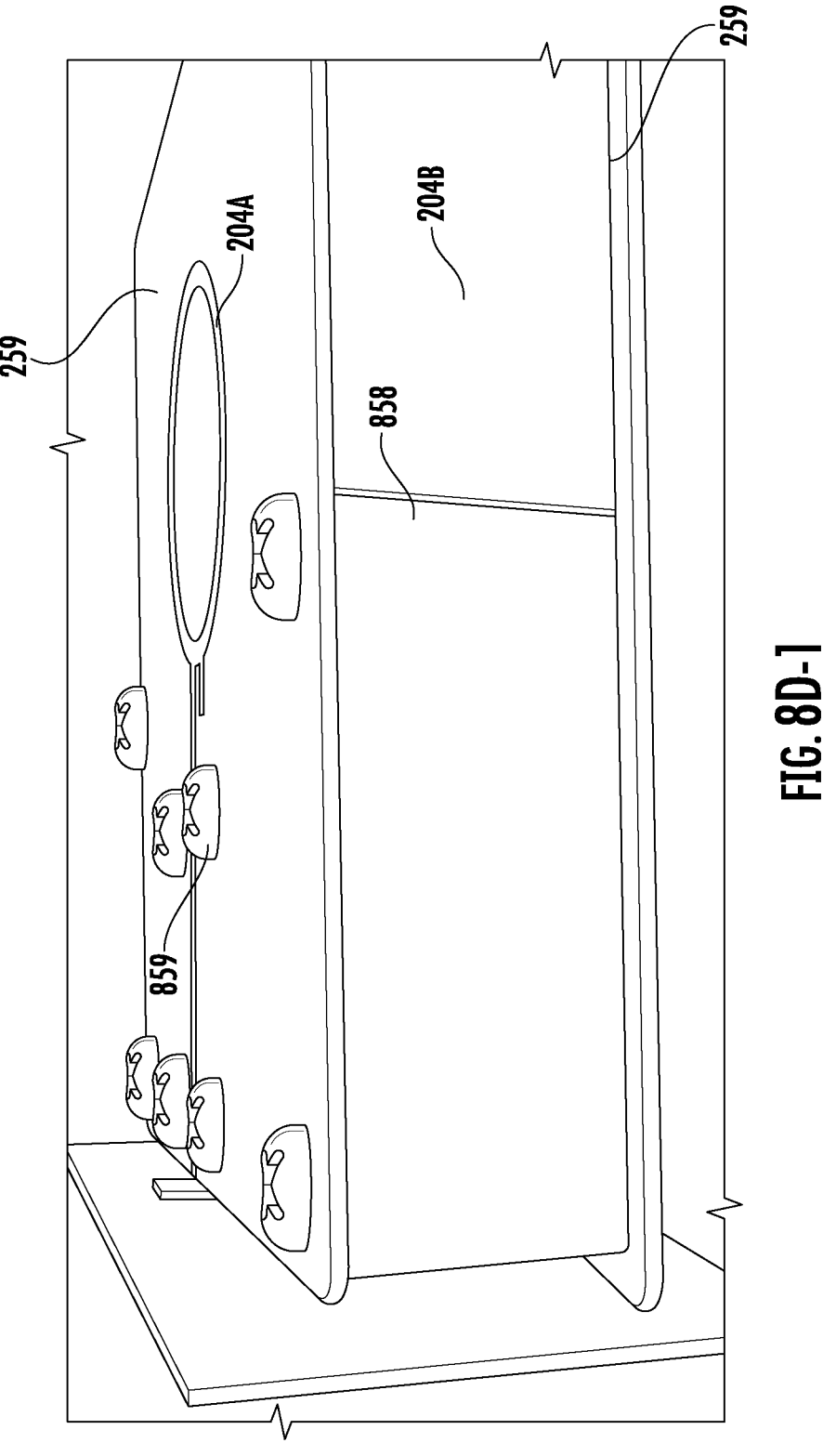
Figures 2, 8D:
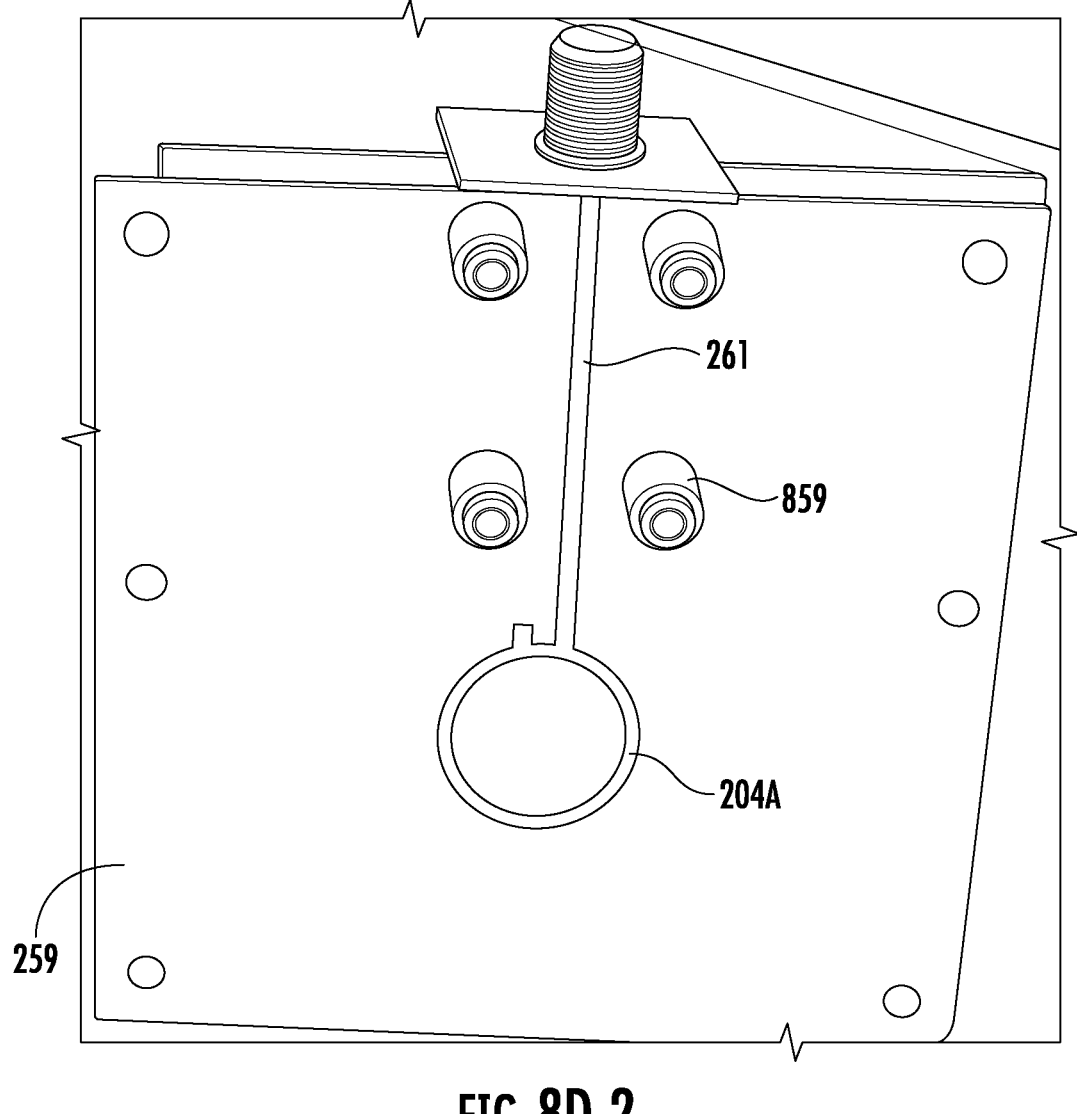
Figures 3, 8D:
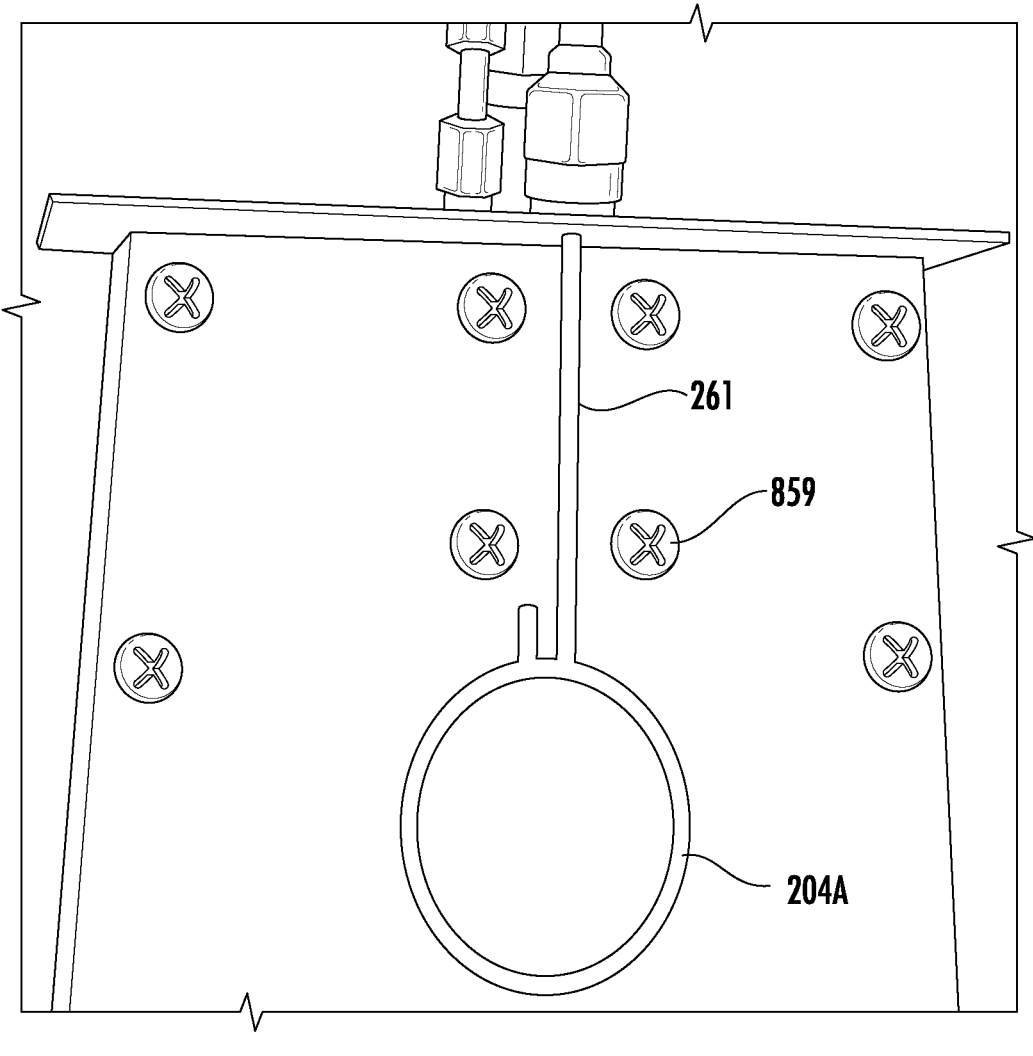
Figures 4, 8D:
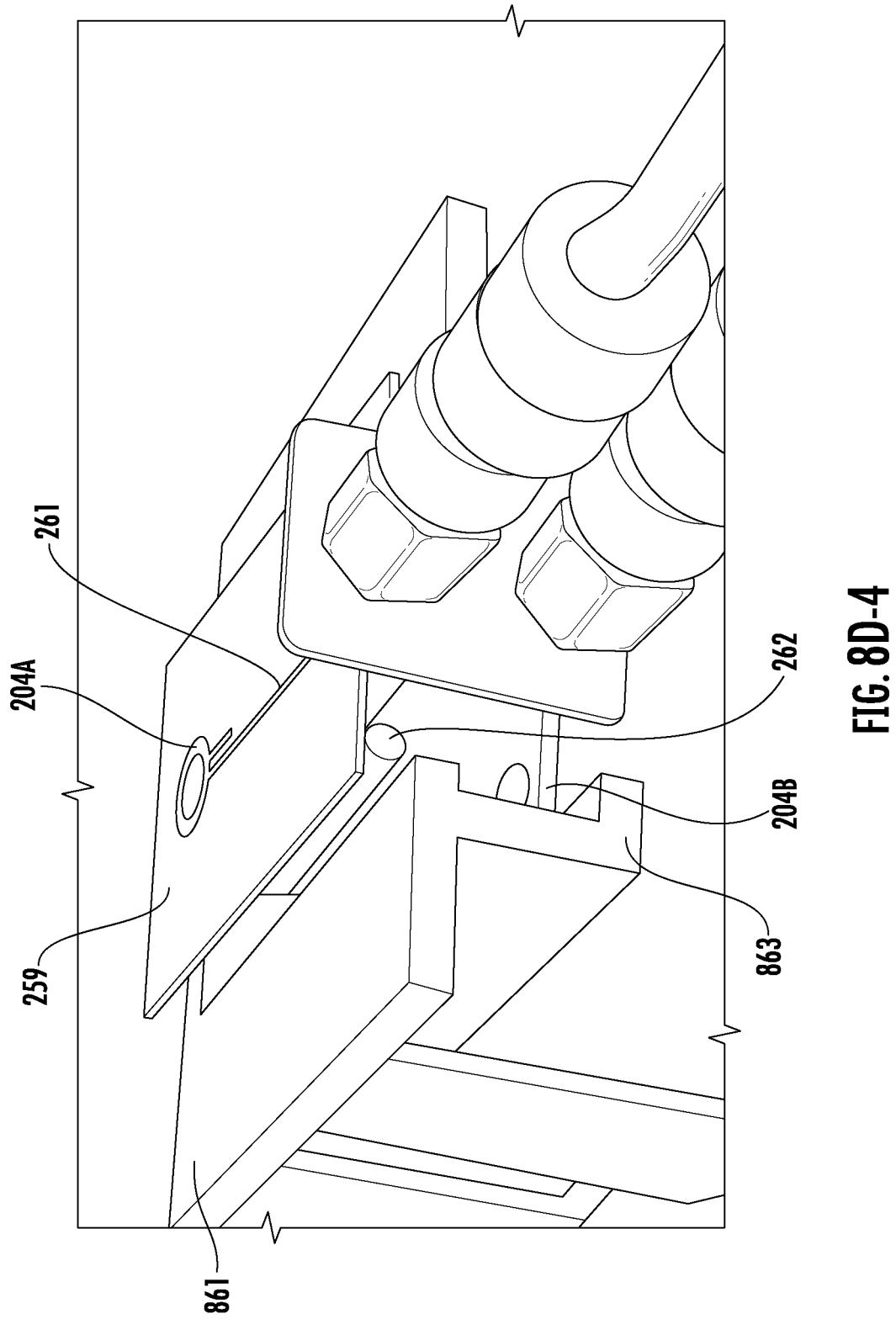

Referring now primarily to FIG. 4, method 250 for measuring at least one confluence value of at least one load including a plurality of cells can include, but is not limited to including, transmitting 251 probe signal 339 (FIG. 1) through calibrated transmission configuration 403 (FIG. 13A). Calibrated transmission configuration 403 (FIG. 13A) can have characteristic impedance 321 (FIG. 1), and calibrated transmission configuration 403 (FIG. 13A) can terminate in at least one load 401 (FIG. 13A) having possibly variable at least one load impedance 101 (FIG. 1). The at least one load 401 (FIG. 13A) can include a plurality of cells 119 (FIG. 2). Method 250 can include measuring 253 reflected signals 337 (FIG. 1) across calibrated transmission configuration 403 (FIG. 13A). Reflected signals 337 (FIG. 1) can be based at least on transmitted probe signal 339 (FIG. 1), and can be caused by an impedance mismatch between characteristic impedance 321 (FIG. 1) and at least one load impedance 101 (FIG. 1). Method 250 can include determining 255 at least one confluence value 327 (FIG. 1) based at least on reflected signals 337 (FIG. 1) associated with at least one load 401 (FIG. 13A).

Figure 5A:
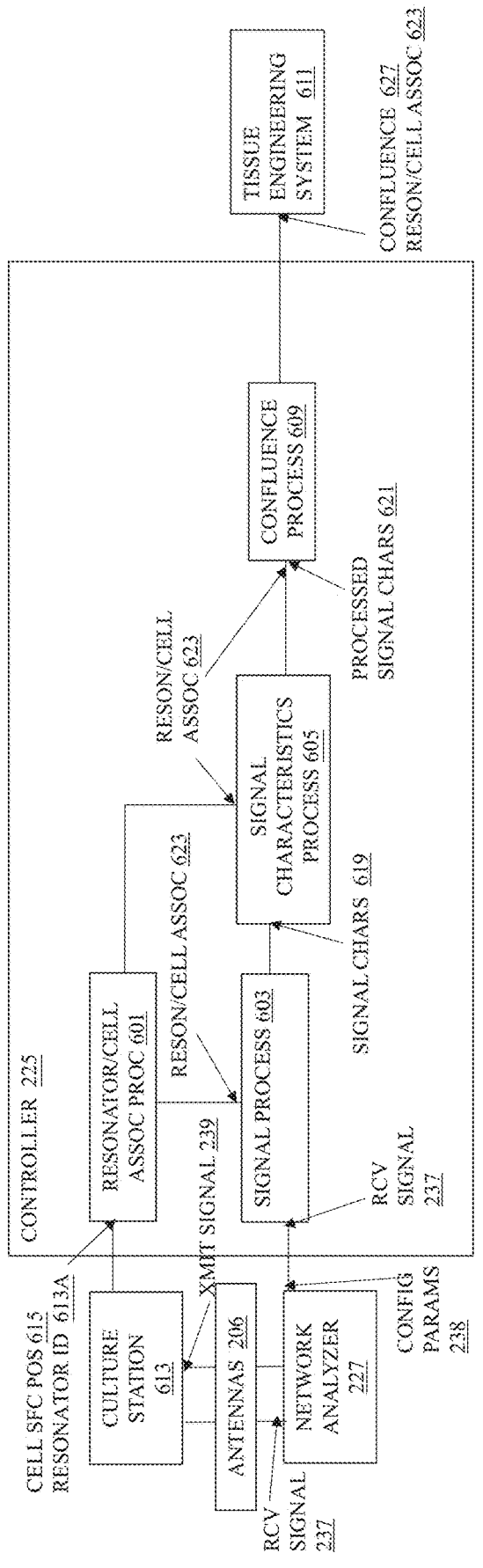
FIGS. 5A and 5B are schematic block diagrams of the components of the control computer of the configurations set out in FIGS. 7B and 7C of the present teachings.

Referring now to FIG. 5A, second configuration confluence system 226 for measuring the confluence of cells wirelessly can include, but is not limited to including, culture station 613, network analyzer 227, and control computer 225. Culture station 613 can provide a structure in which a cell culture surface can reside in the vicinity of at least one resonator. In some configurations, culture station 613 can include a single resonator operably coupled with a single cell culture surface. In some configurations, culture station 613 can include a plurality of resonators operably coupled with at least one cell culture surface. Each of the plurality of operably coupled resonators and cell culture surface pairs in culture station 613 can be, for example, but not limited to, stacked upon each other, seated side-by-side, or vertically positioned adjacent to one another. The at least one cell culture surface can be seeded with cells, and system 226 can optionally ensure that the cells can be near enough to the at least one resonator to have a pre-selected type of effect on the electrical properties of the at least one resonator. The electrical properties can include, but are not limited to including, impedance and resonant frequency. The impedance of the resonator can change over time, for example, based at least on the number and position of the growing cell cultures associated with the resonator.

Continuing to refer to FIG. 5A, control computer 225 can include, but is not limited to including, resonator/cell association process 601 that can identify each resonator, by resonator identification 613A, and cell culture, by cell culture surface position 615, pair. Resonator/cell association process 601 can provide resonator/cell ID 623 to signal process 603, to signal characteristics process 605, and to confluence process 609. Each of the pairs can enable a different response to a nearby signal, the response being based at least on the cell growth happening on the cell culture surface associated with the particular resonator. In some configurations, the response can be based upon the particular geometry of the resonator as well as the cell growth. In some configurations, each resonator/cell surface pair can include, for example, but not limited to, a unique geometry, a unique cell type, a unique number of seeded cells, and a unique cell culture medium composition.

Continuing to refer to FIG. 5A, signal process 603 can provide configuration parameters 238 to network analyzer 227. Network analyzer 227, for example, a conventional vector network analyzer, can be configured to generate a signal having particular signal characteristics, for example, but not limited to, a frequency or a range of frequencies, and can provide signal transmit and receive signals according to a provided or default configuration. Signal process 603 can initiate the generation of at least one signal through network analyzer 227, and network analyzer 227 can generate transmit signal 239. Transmit signal 239 can be propagated and received by antennas 206 in the vicinity of the at least one resonator/cell culture pair seeded with cells in culture station 613. The characteristics of received signal 237 can result from the presence of the at least one resonator/cell culture pair seeded with cells because the resonator can interact with transmit signal 239. Received signal 237 can depend in a substantially predictable way upon the status of the cells associated with the resonator. Signal process 603 can associate transmit signal 239 and received signal 237 with a particular resonator/cell culture surface pair, and can provide signal characteristics 619 to cell characteristics process 605. Signal characteristics 619 can include, but are not limited to including, phase and magnitude as provided by vector network analyzer 227.

Continuing to refer to FIG. 5A, signal characteristics process 605 can process signal characteristics 619, and can provide processed signal characteristics 621 to confluence process 609. Processing of signal characteristics can include, but is not limited to including, determining the impedance and other characteristics of the resonator/cell combination, or in some configurations, for the antenna/resonator/cell combination. Confluence process 609 can calculate confluence 627 based at least on a relationship between processed signal characteristics 621 and confluence 627. In some configurations, the relationship can be empirically determined. Confluence 627 can optionally be provided to, for example, but not limited to, tissue engineering system 611, and can optionally be used in determining the status of growing tissue. System 226 can optionally include a positioner that can determine the placement of the resonator/cell culture surface pair with which the cells are associated in relation to the position of antennas 206 based at least on a pre-selected method for achieving a strong received signal 237.

Figure 5B:
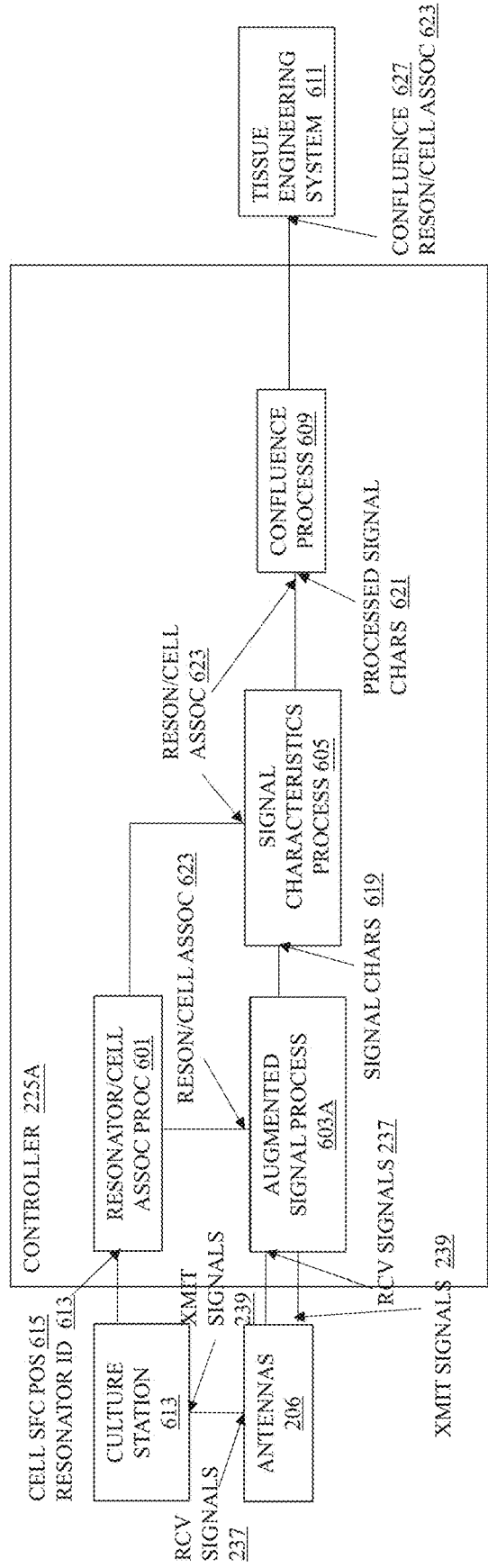

Referring now to FIG. 5B, third configuration system 226A for measuring the confluence of cells can include, but is not limited to including, culture station 613, antennas 206, and integrated controller 225A. Culture station 613 can provide a structure in which a cell culture surface can reside in the vicinity of at least one resonator as described herein. Integrated controller 225A can include, but is not limited to including, resonator/cell association process 601 that can identify each resonator and cell culture surface pair as described herein. Resonator/cell association process 601 can provide resonator/cell ID 623 to augmented signal process 603A, to signal characteristics process 605, and to confluence process 609. Augmented signal process 603A can include signal generation and transmission capabilities that can be configured to mimic at least some aspects of a conventional vector network analyzer. Augmented signal process 603A can be configured to generate a signal having particular signal characteristics, for example, but not limited to, a frequency or a range of frequencies, and can provide signal transmit and receive functions according to a current configuration. Augmented signal process 603 can generate at least one transmit signal 239 and supply that transmit signal to antennas 206, which can behave as described herein. Augmented signal process 603 can receive the received signal 237 from antennas 206. Augmented signal process 603 can associate transmit signal 239 and received signal 237 with a particular resonator/cell culture surface pair, and can provide the signals to processes that can determine confluence 627 as described herein.

Figure 6:
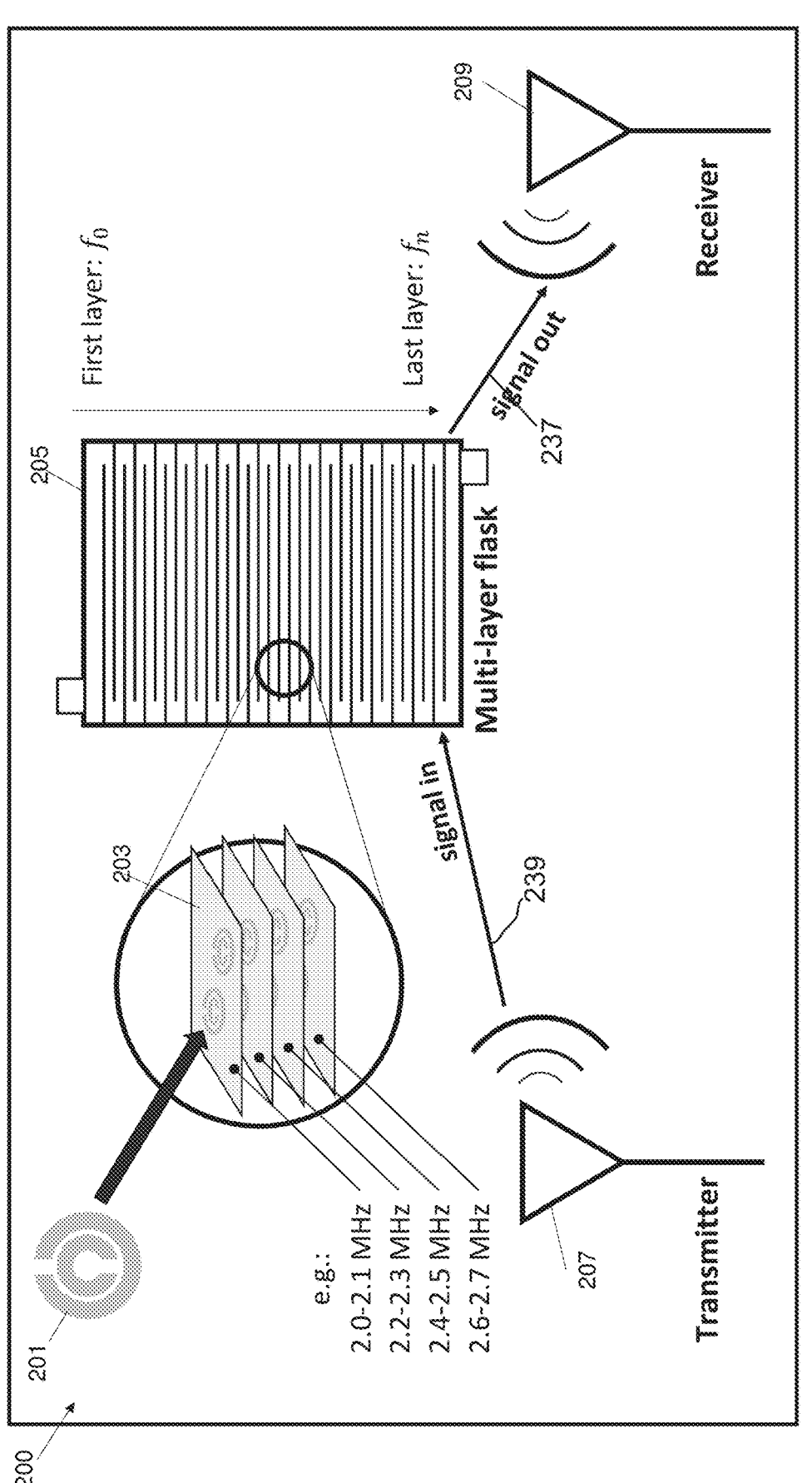
FIG. 6 is a pictorial description of a second configuration system of the present teachings for measuring the confluence of cells including wireless sensing of confluence.

Referring now to FIG. 6, fourth configuration confluence system 200 can wirelessly measure electrical characteristics of at least one resonator 201, by taking advantage of the field interaction properties of the at least one resonator 201 and measuring how they affect an EM signal transmitted by transmitter 207 in the vicinity of resonator 201. Cells, which may proliferate near resonator 201, can act as a dielectric impacting the field interaction properties of the resonator. Confluence 627 (FIG. 5A) of cell cultures can be determined by measuring received signal 237, received by receiver 209, that can result from interaction with resonator 201. In some configurations, system 200 can include, but is not limited to including, multi-layer flask 205 that can include at least one resonator 201. Multi-layer flask 205 can include multiple cell culture surfaces 203, each of which can be associated with at least one resonator 201. In some configurations, at least one resonator 201 can optionally be embedded in cell culture surface 203. In some configurations, each of cell culture surfaces 203 can include resonators 201 that can be tuned to be most sensitive to different particular frequencies of EM energy. In some configurations, all resonators 201 can be tuned to the same frequency. In some configurations, each of resonators 201 or each of groups of resonators 201 can include different geometries, sizes, trace widths, and spacing between traces (see FIGS. 9A,9E). A different resonator design, including, but not limited to, a different geometry, size, and trace width, might be chosen because of, but not limited to, its sensitivity to dielectric changes.

Continuing to refer to FIG. 6, cell culture surface 203 can include any non-cytotoxic material, for example, but not limited to, clear plastic, plasma-treated polystyrene, and untreated polystyrene, to which cells can adhere, and optionally, with which resonator 201 can be integrated. Polystyrene can be treated with surface treatments such as, for example, but not limited to, plasma treatment and gamma radiation, and can optionally be optically clear. Cells 221 (FIG. 7D) and media can be included atop cell culture surface 203 and associated resonator 201. Cell growth in the vicinity of resonators 201 can alter the impedance of resonators 201, and thus received signal 237 (FIG. 7B), in comparison with transmitted signal 239 (FIG. 7B) can indicate cell growth. In some configurations, cell confluence 627 (FIG. 5A) can be determined for a plurality of samples growing on a plurality of cell culture surfaces 203 in multi-layer flask 205. In some configurations, cell culture surface 203 may be created by adhering non-cytotoxic plastic material 2211 (FIG. 7D) to resonator 201 with adhesive 2210 (FIG. 7D) in order to insulate resonator 201 from direct contact with media 223.

Figure 7A:
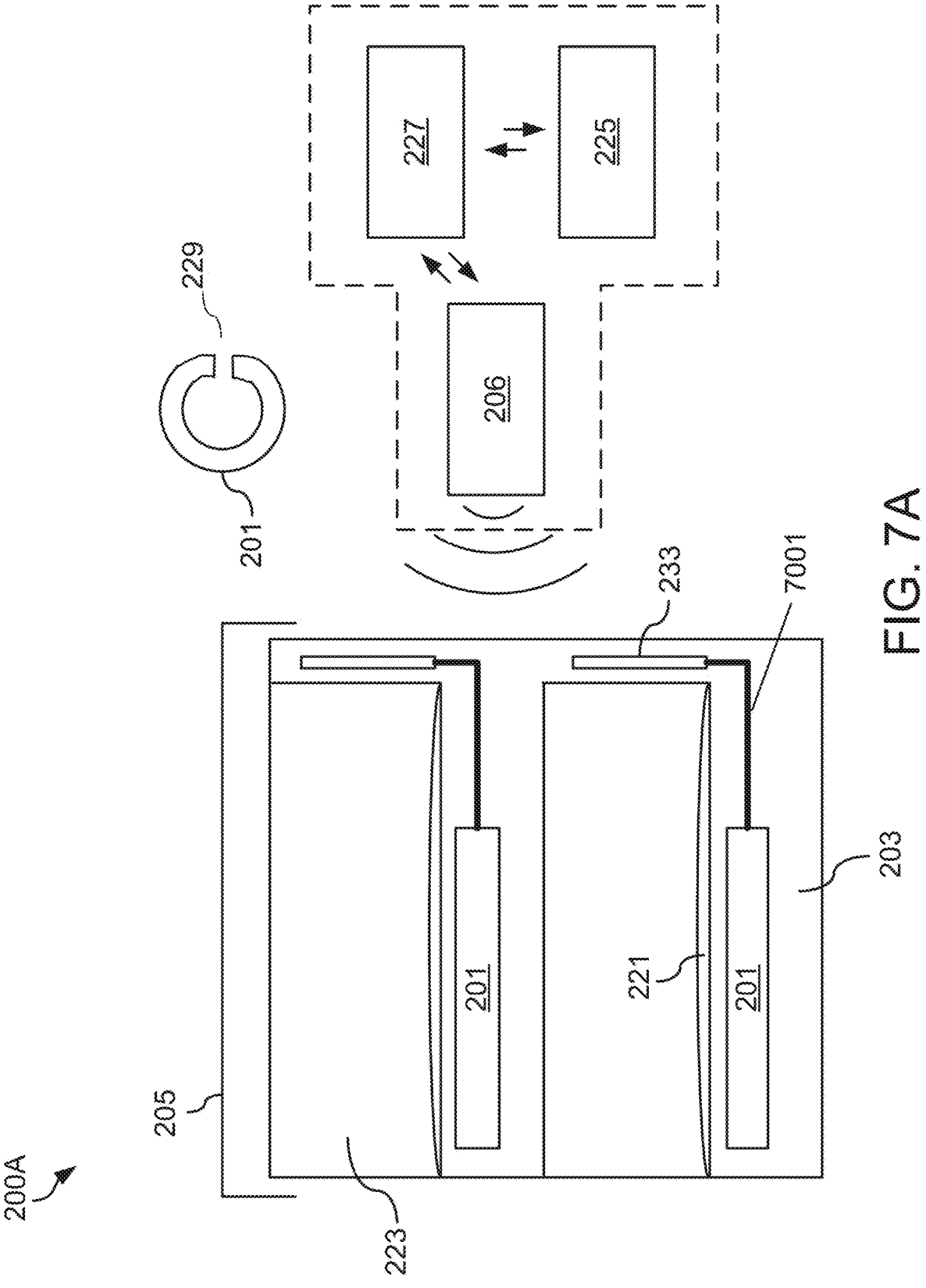
FIG. 7A is a schematic block diagram of the wireless system of the present teachings.
Figure 7B:
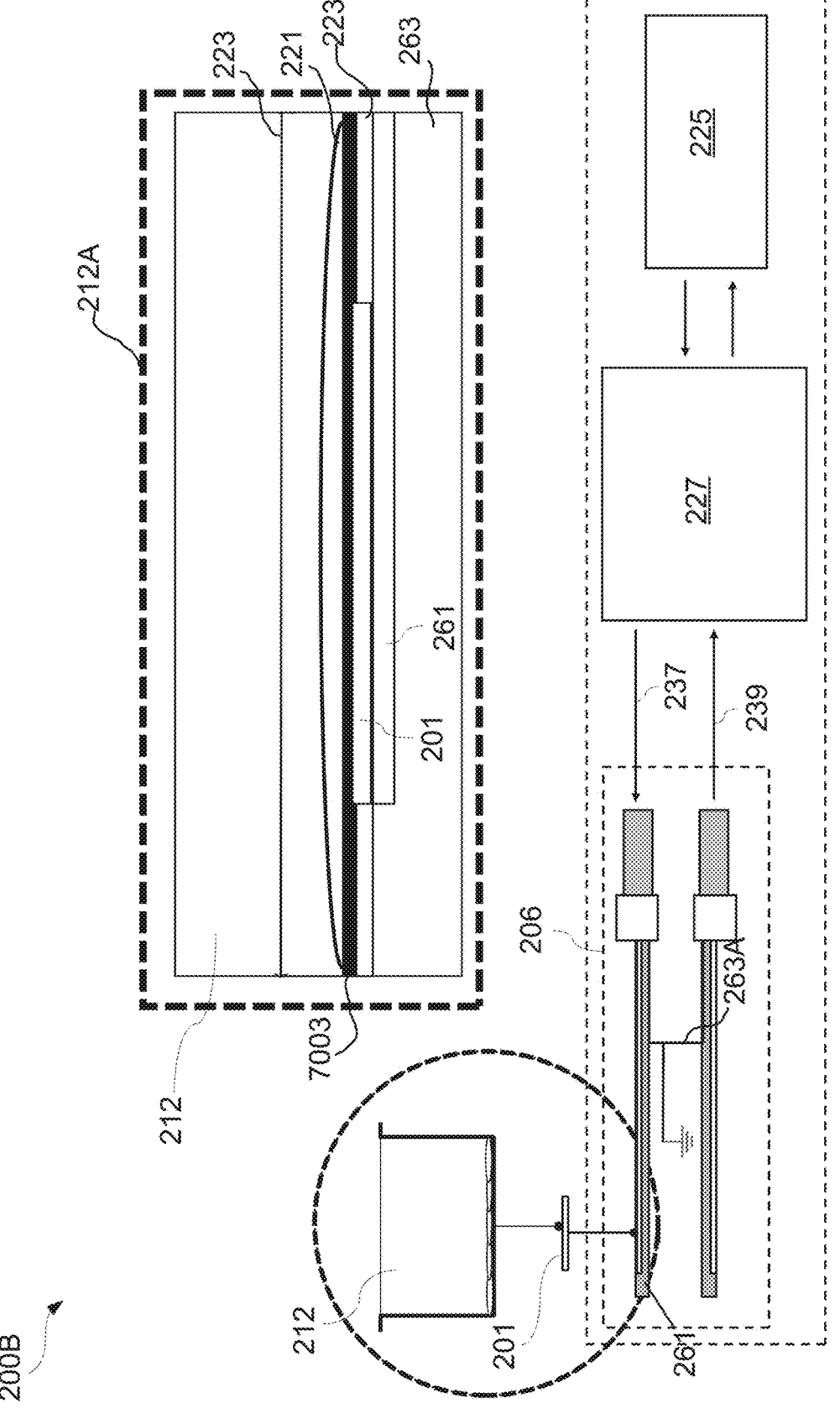
FIGS. 7B and 7C are schematic block diagrams of details of the components of the system of FIG. 7A.
Figure 7C:
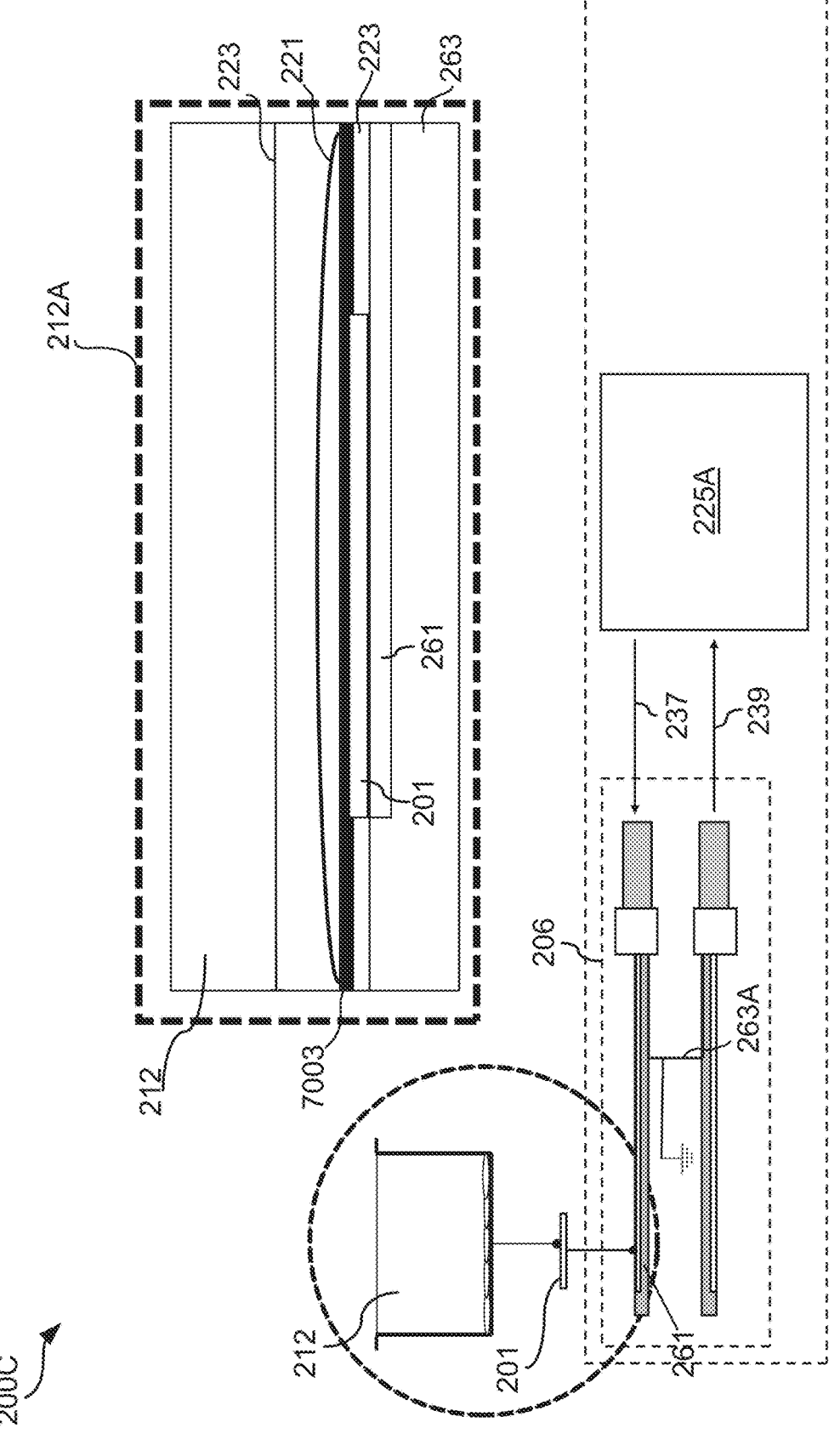
Figure 7D:
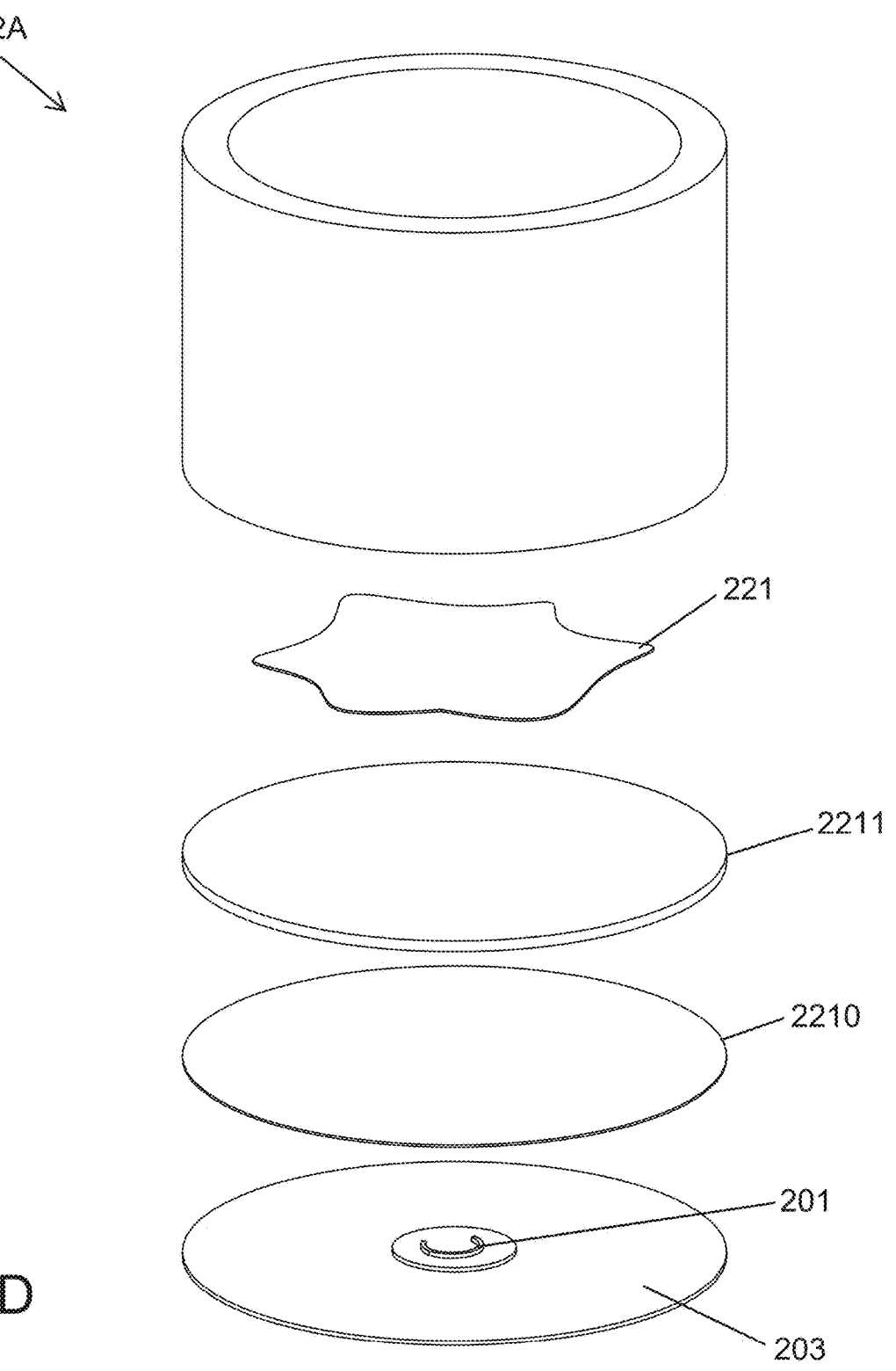
FIGS. 7D and 7E are perspective diagrams of the cell culture well of the present teachings.
Figure 7E:
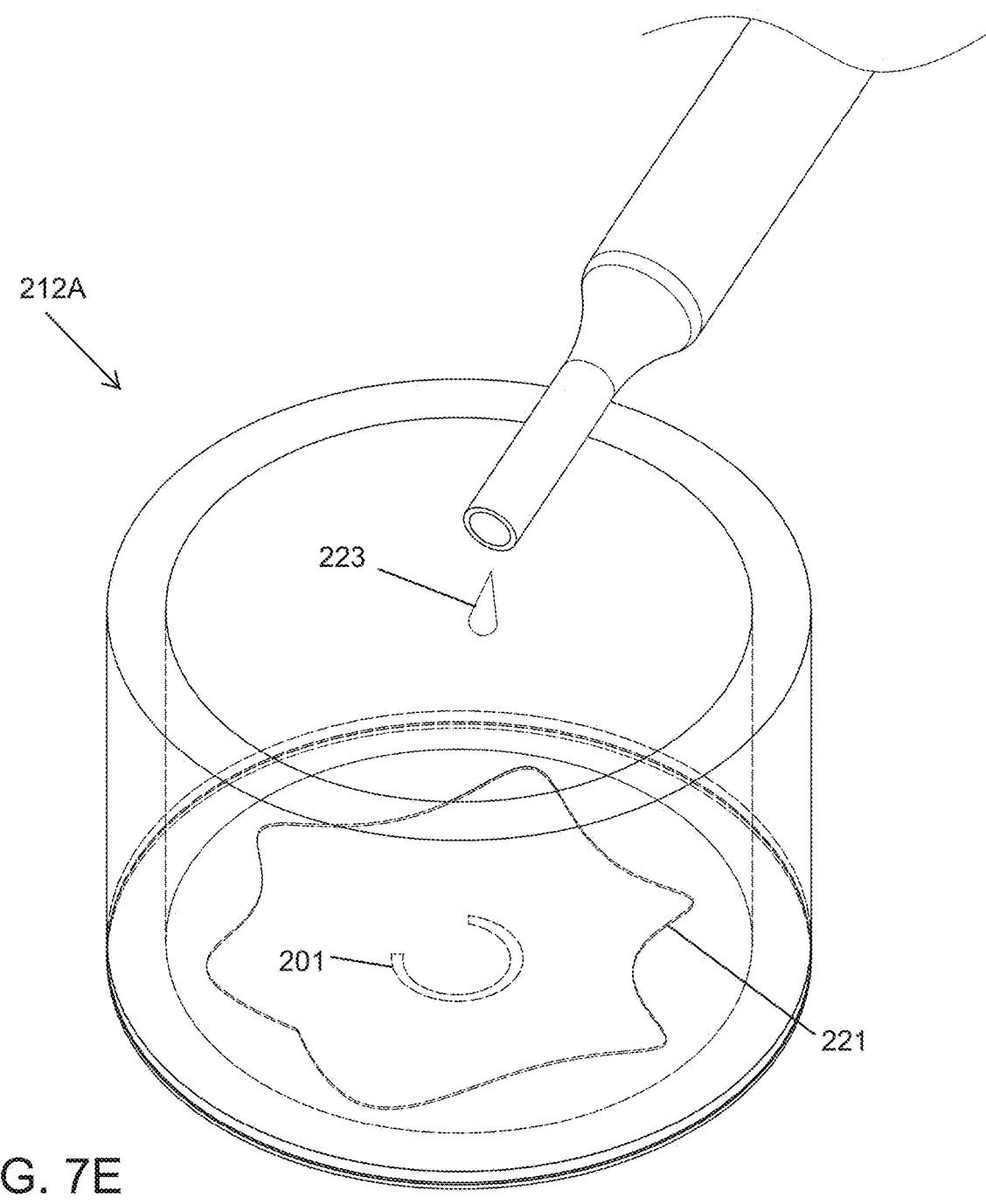

Referring now to FIGS. 7A-7C, fifth configuration confluence system 200A (FIG. 7A), sixth configuration confluence system 200B (FIG. 7B), and seventh configuration confluence system 200C (FIG. 7C) for wirelessly measuring confluence 627 (FIG. 5A) of cells 221 in multi-layer flask 205 (FIG. 7A) can include, but are not limited to including, control computer 225 (FIG. 7A), vector network analyzer 227 (FIG. 7A), antennas 206, and multi-layer flask 205

(FIG. 7A). In some configurations, antenna can include receiver 233 (FIG. 7A) and cabling 7001 (FIG. 7A) Control computer 225 (FIG. 7A) can configure network analyzer 227 (FIG. 7A) by providing, for example, but not limited to, configuration information such as, for example, but not limited to, a frequency sweep range, a number of frequency steps, and a desired power to network analyzer 227 (FIG. 7A). The frequency sweep range can include, but is not limited to including, 9 kHz-3 GHz. The number of frequency steps can be, but is not limited to being, between 800 and 3000. The desired power can be, but is not limited to being, 0 dBm. Vector network analyzer 227 (FIG. 7A) can characterize reflection and transmission responses of RF components, and can quantify magnitude response and phase response. In some configurations, vector network analyzer 227 (FIG. 7A) can include a commercial product such as, for example, but not limited to, Copper Mountain Technologies S5085 VNA. In some configurations, vector network analyzer 227 (FIGS. 7A/7B) can be controlled manually. In some configurations, such as, for example, but not limited to, seventh configuration confluence system 200C (FIG. 7C), integrated controller 225A (FIG. 7C) can include at least some of the functionality of both control computer 225 (FIGS. 7A/7B) and vector network analyzer 227 (FIGS. 7A/7B). Vector network analyzer 227 (FIGS. 7A/7B) or integrated controller 225A (FIG. 7C) can generate a known stimulus EM signal 239 (FIG. 7B) that can travel through antennas 206 in the vicinity of resonator 201 associated with cells 221. In some configurations, antennas 206 can include ground 263A (FIG. 7B). Resonator 201 interacts differently with EM signal 239 based on the growth status of cells 221, changing return signal 237 (FIG. 7B), which is received by vector network analyzer 227 (FIG. 7B). The response of resonator 201, ultimately embodied in signal 237 (FIG. 7B), can be processed by control computer 225 (FIG. 7B) or integrated controller 225A (FIG. 7C). In some configurations, network analyzer 227 (FIG. 7B) and/or control computer 225 (FIG. 7B), or integrated control computer 225A (FIG. 7C) can extract metrics from signal 237 (FIG. 7B), including, but not limited to, scattering parameters, return loss, and insertion loss. Changes in these metrics can processed by control computer 225 (FIG. 7B) or integrated controller 225A (FIG. 7C) to indicate cell confluence.

Continuing to refer to FIGS. 7A-7C, resonator 201 can include any conductive trace that embodies some inductance and some capacitance. The capacitance may be embodied by, but is not limited to being embodied by, air gap 229 (FIG. 7A). In some configurations, membrane 7003 (FIG. 7B) can overlie resonator 201 and underlie cells 221

Continuing to refer to FIGS. 7A-7C, in some configurations, growth media 223 (also called "cell culture media") can include nutrient formulations made for specific types of cells 221. Requirements for cells 221 to grow and thrive can include, but are not limited to including, controlled temperature, a surface for cell attachment such as, for example, cell culture surface 203 (FIG. 7A), and growth media 223 that can maintain, for example, but not limited to, the correct pH. Growth media 223 can include a liquid or gel designed to support the growth of cells 221. Growth media 223 can include, for example, but not limited to, amino acids, vitamins, inorganic salts, glucose, and serum as a source of growth factors, hormones, and attachment factors. Cells 221 and growth media 223 in flask 212, enlarged flask 212A, can possess dielectric properties that can affect the confluence measurement, using the present teachings, of cells 221. In some configurations, the dielectric properties of growth media 223 can include, but are not limited to including, a dielectric constant in approximately the range of 75-80. In some configurations, the dielectric properties of cells 221 can include, but are not limited to including, a dielectric constant in approximately the range of 30-60.

Referring now to FIGS. 8A through 8D-5, in some configurations, antennas 206 (FIG. 7B) can include, but are not limited to including, loop antennas, dipole antennas, horn antennas, and/or corner reflector antennas. In some configurations, the size of loop antenna 204 can be chosen based on, but is not limited to being based on, having a low return loss in a desired frequency range. In some configurations, the resonator can be coupled to the antenna, and the collective antenna-resonator system can have a resonant frequency. In some configurations, this resonant frequency can be approximately in the range of 1.6-2 GHz, depending upon the dielectric properties of cells 221 and media 223 (FIGS. 7B-C). In some configurations, loop antenna dimensions can include interior loop diameter 251 (FIG. 8A) in the range of about 0.15-1.0 inch, and exterior loop diameter 253 (FIG. 8A) in the range of about 0.24-1.1 inch, trace width 257 (FIG. 8A) in the range of about 0.03-0.07 inches, exterior length 255 (FIG. 8A) in the range of about 0.27-1.3 inch, and gap 229 (FIG. 8A) in the range of about 0.02-0.05 inch. These measurements are exemplary only. Loop antennas 851/853/855 (FIGS. 8A-1, 8A-2) include relatively small-, medium-, and large-dimensioned loops.

Referring now to FIGS. 8B-8D, loop antenna 204 can be mounted upon printed circuit board (PCB) substrate 259 (FIG. 8B), and can include transmission trace 261 (FIG. 8B) that can operably connect with network analyzer 227 (FIG. 7A) and/or integrated controller 225A (FIG. 7C). PCB substrate 259 (FIG. 8B) can include, for example, but not limited to, flame retardant fiberglass, phenolics, and epoxies of any thickness suitable to allowing signals to flow between antennas 206 (FIG. 7B), of which loop antenna 204 is an example. Ground 263 (FIG. 8C) can include, but is not limited to including, copper or copper-clad ground plane that can reflect radio waves from other antenna elements. Ground 263 can include, for example, but not limited to, a conducting surface whose size depends upon the wavelength of the radio waves. In some configurations, ground 263 can cover a great deal of substrate 259 (FIG. 8B), underlying transmission trace 261 (FIG. 8B). In some configurations, transmission trace 261 (FIG. 8B) can include a microstrip, a coplanar wave guide, and/or a strip line.

Referring now to FIGS. 8D-1, 8D-2, and 8D-3, in some configurations, antennas 204A/204B (FIG. 8D-1) can be separated by a space approximately an inch or less. In the separation space, ground block 858 (FIG. 8D-1) can provide grounding between antennas 204A/204B (FIG. 8D-1). Fasteners 859 (FIGS. 8D-2. 8D-3) can ensure both mechanical stability and a more robust electrical connection between the grounds of antennas 204A/204B (FIG. 8D-1) and ground block 858 (FIG. 8D-1). Stability and a robust ground connection can be necessary to reduce spurious signals during cell confluence detection. In some configurations, fasteners 859 (FIGS. 8D-2, 8D-3) can be positioned at a pre-selected distance from trace 261 (FIGS. 8D-2, 8D-3). The pre-selected distance can be chosen based at least on stability requirements dictated at least by the materials with which PCB substrate 259 is constructed, the width of trace 261 (FIGS. 8D-2, 8D-3), the material with which trace 261 (FIGS. 8D-2, 8D-3) is constructed, and the material with which ground 263 (FIG. 8C) and ground block 858 (FIG. 8D-1) are constructed. In some configurations, ground block 858 could be replaced with a conductive sheet 262 (FIG.

8D-4) and soldered to the grounds of antennas 204A/204B (FIG. 8D-1) instead of using fasteners 859 (FIGS. 8D-2, 8D-3).

Antenna 204A, for example, can transmit signal 239 (FIG. 7B) from network analyzer 227 (FIG. 7B) to antenna 204B (FIG. 8D) or receive signal 237 (FIG. 7B) from Antenna 204B (FIG. 8D) and convey it to network analyzer 227 (FIG. 7B). Antenna 204B (FIG. 8D), for example, can receive signal 237 (FIG. 7B) from Antenna 204A (FIG. 8D) and convey it to network analyzer 227 (FIG. 7B) or transmit signal 239 (FIG. 7B) from network analyzer 227 (FIG. 7B) to antenna 204A (FIG. 8D). In some configurations, a single antenna 204A/204B (FIG. 8D) can both receive signal 239 (FIG. 7B) from network analyzer 227 (FIG. 7B) and also convey signal 237 (FIG. 7B) back to network analyzer 227 (FIG. 7B).

Figures 5, 8D:
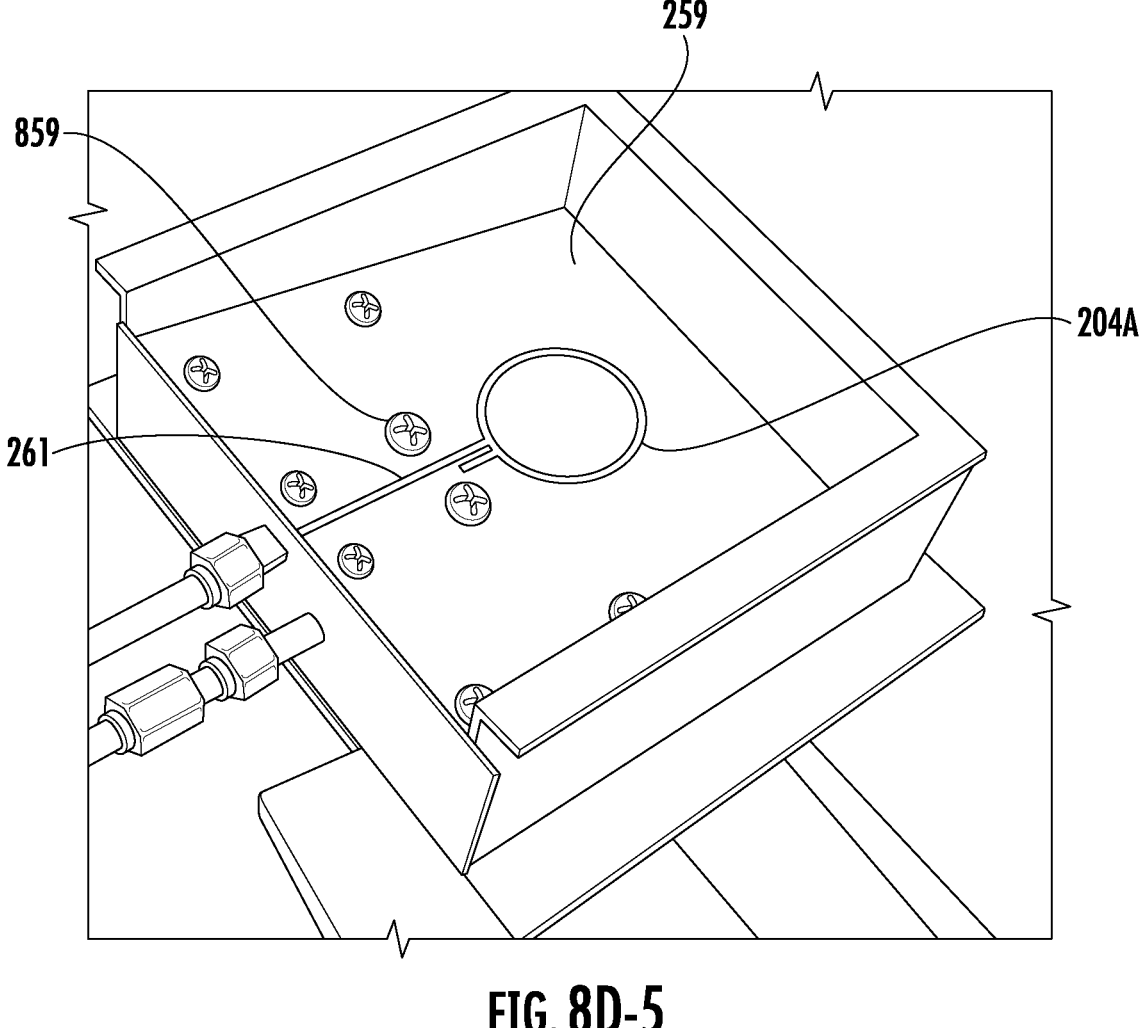

Referring now to FIGS. 8D-4 and 8D-5, antennas 204A/ 204B (FIG. 8D-4) can be oriented in any way that can enable strong signal transfer. Enclosing antennas 204A/204B (FIG. 8D-4) in enclosure 861 improves the mechanical stability of the system. Enclosure 861 can be constructed to receive antennas 204A/204B (FIG. 8D-4) within tabs 863 (FIG. 8D-4). Tabs 863 (FIG. 8D-4) can be spaced according to the pre-selected spacing between antennas 204A/204B (FIG. 8D-4), when used.

Figure 9A:
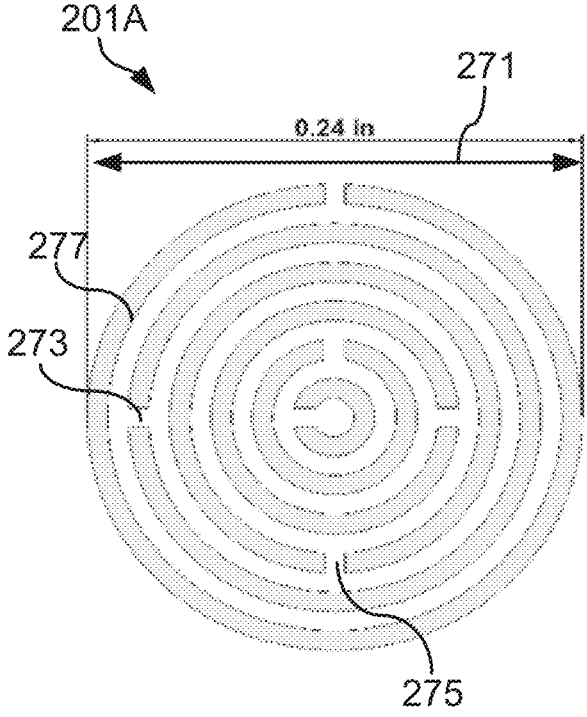
FIG. 9A is a pictorial diagram of a configuration of the resonator of the present teachings.
Figure 9B:
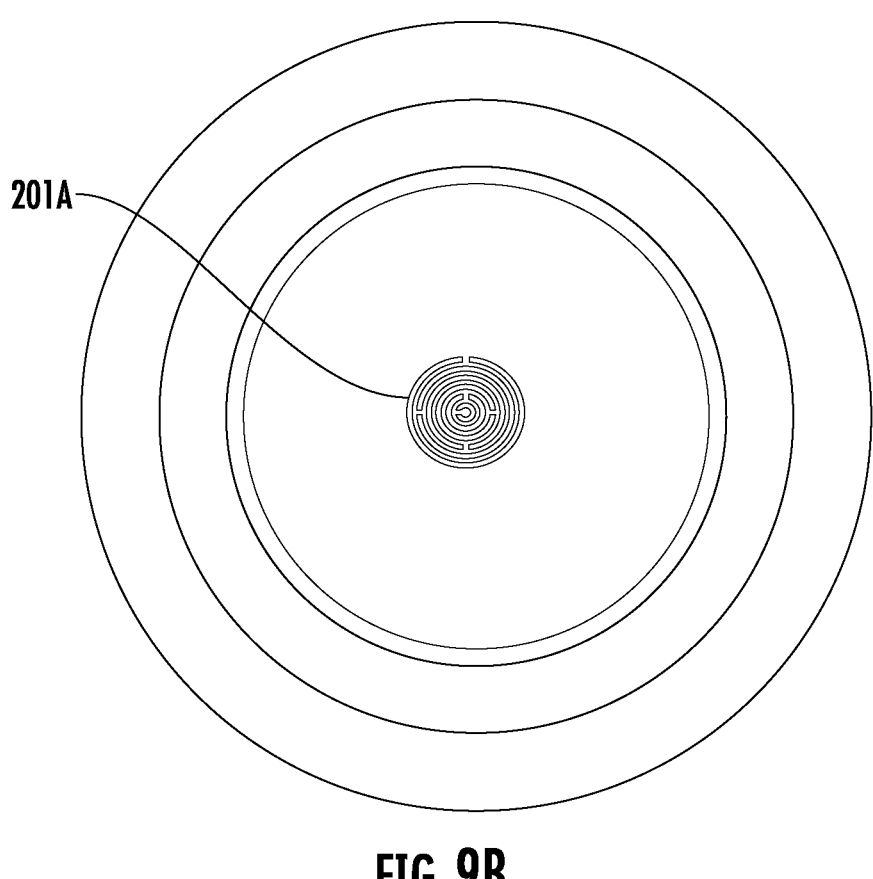
FIG. 9B is a photograph of the configuration of the resonator of FIG. 9A.

Referring now to FIGS. 9A and 9E, resonator 201 (FIG. 7A) can include various shapes and sizes. The shapes and sizes described herein are exemplary only. In some configurations, resonator 201A (FIGS. 9A, 9E) can include, for example, a plurality of turns 277 (FIG. 9A) and a plurality of gaps 273/275 (FIG. 9A), where gaps 273/275/etc. (FIG. 9A) can be, for example, but not limited to, oriented at 90° with respect to each other. In some configurations, resonator 201A can include, for example, diameter 271 of about 0.24 inch. Resonator 201A could be used when field uniformity over the surface of the resonator and the ability to resolve resonance under water, including water containing electrolytes and other substances, is important.

Figure 10:
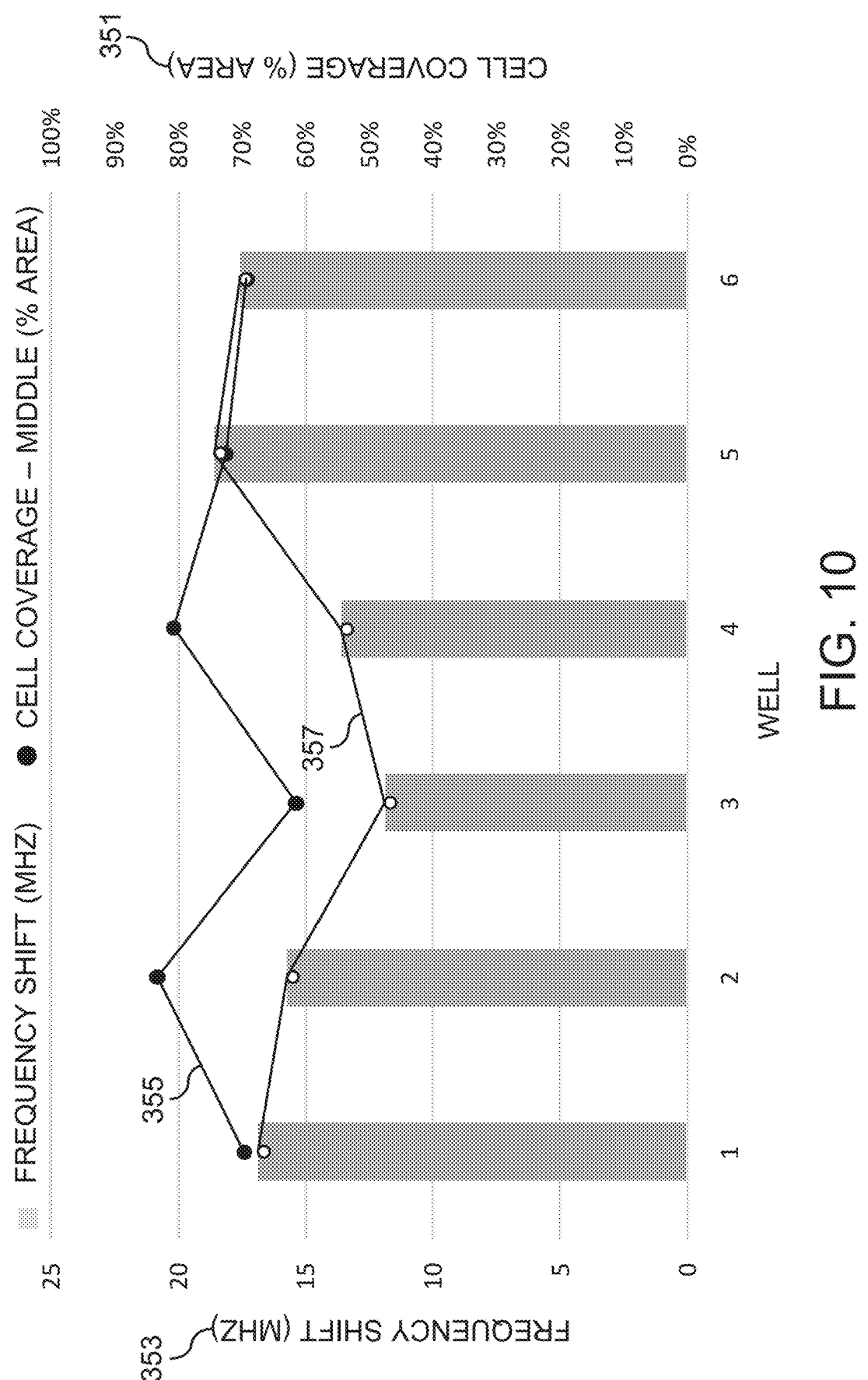
FIG. 10 is a graphical diagram of cell discrimination demonstrated using the system of the present teachings.
Figure 11:
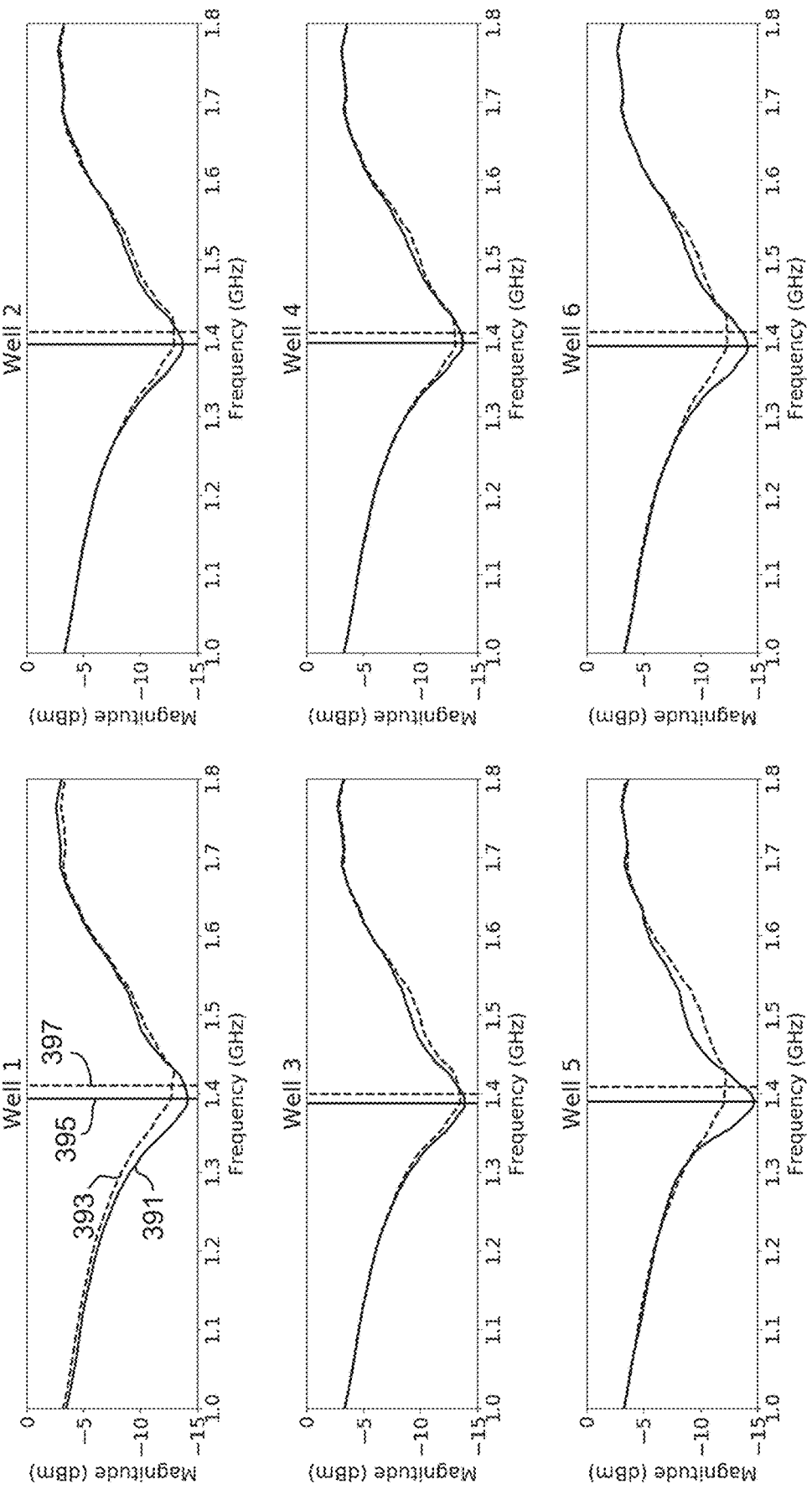
FIG. 11 is a graphical diagram of resonant frequency shifting between cell and no-cell samples using the system of the present teachings.

Referring now to FIGS. 10 and 11, in a six-well experiment, cell coverage 351 (FIG. 10) and signal characteristics such as, for example, but not limited to, frequency shift 353 (FIG. 10) measurements can verify that system 200 (FIG. 7B) can discriminate between samples depending on cell coverage. Cell coverage 355 (FIG. 10) approximately follows frequency shift 357 (FIG. 10), indicating that frequency shift 353 (FIG. 10) measured by system 200 (FIG. 7B) approximately indicates the measured cell coverage 355. For each sample in the experiment of FIG. 10, pre-cell growth measurements 391 (FIG. 11) of frequency and post-cell growth measurements 393 (FIG. 11) indicate frequency shift 357 (FIG. 10). The frequency response can be visually identified by the distance between approximate magnitude minima 395 (FIG. 11) and 397 (FIG. 11).

Referring now to FIG. 12, method 150 for measuring the confluence of cells can include, but is not limited to including, associating 151 at least one resonator with at least one cell culture surface. The at least one cell culture surface can be seeded with a plurality of cells, and the plurality of cells can be positioned near enough to the at least one resonator to affect at least one electrical property of the at least one resonator. Method 150 can include generating 153 at least one electromagnetic (EM) signal. The at least one EM signal can propagate in the vicinity of the at least one resonator, and the at least one resonator can interact with at least part of the EM signal. Method 150 can include receiving 155 at least one signal resulting from the generated at least one signal as affected by the at least one resonator, and processing 157 received signal characteristics of the received at least one signal with respect to generated signal characteristics of the generated at least one EM signal. Method 150 can include calculating 159 confluence based at least on a pre-selected relationship between the confluence and the processed received signal characteristics.

Referring now to FIGS. 13A and 13B, first configuration confluence system 125 (FIG. 1), depicted in overview in FIG. 13A, and second configuration confluence system 200 (FIG. 6), depicted in overview in FIG. 13B, while both relying on probing cells with signals, differ in geometry and components. First configuration confluence system 125 can determine confluence 327 (FIG. 1) based at least upon reflection 337 (FIG. 13A) of transmitted signal 339 (FIG. 13A) along calibrated transmission configuration 403 (FIG. 13A). Reflection 377 (FIG. 13A) can depend at least upon the characteristics of signal 339 (FIG. 13A), load 401 (FIG. 13A) (including cells), and calibrated transmission configuration 403 (FIG. 13A). As cells grow, the characteristics of load 401 (FIG. 13A) can change, for example, but not limited to, there could be a change of impedance 101 (FIG. 1). In some configurations, first configuration confluence system 125 (FIG. 1) can measure confluence based at least on reflection 337 (FIG. 13A). On the other hand, second configuration confluence system 200 (FIG. 6) can determine confluence 627 (FIG. 5A) based at least on the changes between wirelessly transmitted EM signal 237 (FIG. 13B) and wirelessly received EM signal 239 (FIG. 13B). In second configuration confluence system 200 (FIG. 6), as transmitted EM signal 237 (FIG. 13B) encounters resonator 201 (FIG. 13B), and resonator 201 (FIG. 13B) can interact with transmitted EM signal 237 (FIG. 13B). Received EM signal 239 (FIG. 13B) can result, at least in part, from interaction between signal 237 and resonator 201. As cells grow, resonator 201 (FIG. 13B), which can be placed in the vicinity of the growing cells, can interact varyingly with signal 237, and received signal 239 (FIG. 13B) can include characteristics that indicate effects of cell growth on the signal interactions (FIG. 13B). Confluence can be determined by determining at least one characteristic of received signal 239 (FIG. 13B) relative to transmitted signal 237 (FIG. 13B), and relating the at least one characteristic to confluence. In some configurations, the confluence can be based at least on received signal 239 (FIG. 13B). In some configurations, system 125 (FIG. 1), system 200 (FIG. 6), and systems 200A/B/C (FIGS. 7A/B/C) can be used to monitor tissue development, including the thickness of extracellular matrix. In some configurations, modifications of system 125 (FIG. 1), system 200 (FIG. 6), and systems 200A/B/C (FIGS. 7A/B/C) can be used to sense levels of liquid and very small movements of objects, smaller than a thousandth of an inch. Sensing levels of liquid can include embedding at least one resonator on a surface of a vessel holding the fluid, and subjecting the resonator to at least one EM signal, resulting in received signal characteristics. The height of the liquid can be based on the received signal characteristics. Sensing object movement can include embedding at least one resonator in an object that is moved from a first position to a second position. The at least one resonator can be subjected to at least one EM signal when the object is in the first position and again when the object is in the second position, producing two sets of resulting signal characteristics. The distance that the object is moved can be based on comparing the two sets of the resulting signal characteristics.

Configurations of the present teachings are directed to computer systems for accomplishing the methods discussed in the description herein, and to computer readable media containing programs for accomplishing these methods. The raw data and results can be stored for future retrieval and processing, printed, displayed, transferred to another computer, and/or transferred elsewhere. Parts of system 125 (FIG. 1), system 226 (FIG. 5A), system 226A (FIG. 5B), system 200 (FIG. 6), system 200A (FIG. 7A) system 200B (FIG. 7B), and system 200C (FIG. 7C), for example, can execute on a computer having a variable number of CPUs. Other alternative computer platforms can be used.

The present configuration is also directed to hardware, firmware, and software for accomplishing the methods discussed herein, and computer readable media storing software for accomplishing these methods. The various modules described herein can be accomplished by the same CPU, or can be accomplished on a different computer. In compliance with the statute, the present configuration has been described in language more or less specific as to structural and methodical features. It is to be understood, however, that the present configuration is not limited to the specific features shown and described.

Methods 250 (FIG. 4) and 150 (FIG. 12), can be, in whole or in part, implemented electronically. Signals representing actions taken by elements of system 125 (FIG. 1), system 226 (FIG. 5A), system 226A (FIG. 5B), system 200 (FIG. 6), system 200A (FIG. 7A) system 200B (FIG. 7B), for example, and other disclosed configurations can travel over at least one live communications network. Control and data information can be electronically executed and stored on at least one computer-readable medium. The systems can be implemented to execute on at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form, subject to appropriate licenses where necessary, including, but not limited to, Graphic Interchange Format (GIF), Joint Photographic Experts Group (JPEG), Portable Network Graphics (PNG), Scalable Vector Graphics (SVG), and Tagged Image File Format (TIFF).

While the present teachings have been described above in terms of specific configurations, it is to be understood that they are not limited to these disclosed configurations. Many modifications and other configurations will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A method for measuring at least one metric of at least one cell culture that is accumulating or shedding biological material, the method comprising:

transmitting a signal through a calibrated transmission configuration, the calibrated transmission configuration having a characteristic impedance, the calibrated transmission configuration terminating in at least one biological cell culture having a first impedance;

measuring reflection in the calibrated transmission configuration, the reflection based at least on the transmitted signal, the reflection being caused by an impedance mismatch between the characteristic impedance and the first impedance;

following the measuring of the reflection of the signal, transmitting, a second signal through the calibrated transmission configuration, the least one biological cell culture having a second impedance;

measuring a second reflection in the calibrated transmission configuration, the second reflection being caused by an impedance mismatch between the characteristic impedance and the second impedance; and determining the at least one metric relating to the biological material based at least on a comparison between the first and second reflections associated with the at least one biological cell culture.

2. The method as in claim 1 wherein the at least one biological cell culture comprises growth media, the growth media having a media impedance.

3. The method as in claim 1 wherein the calibrated transmission configuration comprises:

a transmission line having a first end and a second end, a first connector operably coupling the first end with at least one probe associated with the at least one biological cell culture, and a second connector operably coupling the second end with the control computer, the control computer performing the measuring the reflected signals and the determining at least one confluence value of cells.

4. The method as in claim 1 further comprising:

a reflection process associating the at least one biological cell culture with at least one culture identifier.

5. The method as in claim 1 wherein the material comprises cells, the cells having a cell-specific impedance.

6. The method as in claim 5 further comprising:

determining the at least one metric by subtracting the cell-specific impedance from the characteristic impedance.

* * * * *